「12」 United States Patent
Anand et al.

(10) Patent No.: US 10,988,766 B2
(45) Date of Patent: Apr. 27, 2021

(54) COMPOSITIONS AND METHODS USED IN DIAGNOSING AND TREATING COLORECTAL CANCER

(71) Applicant: Oregon Health & Science University, Portland, OR (US)

(72) Inventors: Sudarshan Anand, Portland, OR (US); Liana Tsikitis, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 16/475,996

(22) PCT Filed: Jan. 5, 2018

(86) PCT No.: PCT/US2018/012696
§ 371 (c)(1),
(2) Date: Jul. 3, 2019

(87) PCT Pub. No.: WO2018/129402
PCT Pub. Date: Jul. 12, 2018

(65) Prior Publication Data
US 2019/0330632 A1    Oct. 31, 2019

Related U.S. Application Data

(60) Provisional application No. 62/443,129, filed on Jan. 6, 2017.

(51) Int. Cl.
| C12N 15/113 | (2010.01) |
| A61P 35/00 | (2006.01) |
| A61K 31/513 | (2006.01) |
| A61K 31/713 | (2006.01) |
| A61K 45/06 | (2006.01) |
| C12Q 1/6886 | (2018.01) |

(52) U.S. Cl.
CPC .......... *C12N 15/113* (2013.01); *A61K 31/513* (2013.01); *A61K 31/713* (2013.01); *A61K 45/06* (2013.01); *A61P 35/00* (2018.01); *C12Q 1/6886* (2013.01); *C12N 2310/141* (2013.01); *C12Q 2600/106* (2013.01); *C12Q 2600/178* (2013.01)

(58) Field of Classification Search
None
See application file for complete search history.

(56) References Cited

U.S. PATENT DOCUMENTS

| 9,242,000 B2 | 1/2016 | Cheresh et al. |
| 2014/0341841 A1 | 11/2014 | Jacob et al. |
| 2016/0068841 A1 | 3/2016 | Leschinsky |
| 2017/0362590 A1 | 12/2017 | Anand et al. |

OTHER PUBLICATIONS

Giantonio et al. Journal of Clinical Oncology Vo. 25, No. 12 Apr. 2007 pp. 1539-1544.*
Yang, Hong, et al. "Antitumor activity of BRAF inhibitor vemurafenib in preclinical models of BRAF-mutant colorectal cancer." Cancer research 72.3 (2012): 779-789.*
Burrell et al., Replication stress links structural and numerical cancer chromosomal instability, Nature, vol. 494, 492-496 (2013).
Cano et al., The RNA-binding E3 ubiquitin ligase MEX-3C links ubiquitination with MHC-I mRNA degradation, EMBO Journal (2012), 31, 3596-3606.
Eschrich et al., A Gene Expression Model of Intrinsic Tumor Radiosensitivity: Prediction of Response and Prognosis After Chemoradiation, Int. J. Radiation Oncology Biol. Phys., vol. 75, No. 2, pp. 489-496, 2009.
Hughes-Davies et al., EMSY Links the BRCA2 Pathway to Sporadic Breast and Ovarian Cancer, Cell, vol. 115, 523-535, Nov. 26, 2003.
Jonker et al., Epiregulin gene expression as a biomarker of benefit from cetuximab in the treatment of advanced colorectal cancer, British Journal of Cancer (2014) 110, 648-655.
Kanaan et al., A Plasma MicroRNA Panel for Detection of Colorectal Adenomas a Step Toward More Precise Screening for Colorectal Cancer, Ann Surg 2013;258:400-408.
Li et al., Circulating miR-25-3p and miR-451a May be Potential Biomarkers for the Diagnosis of Papillary Thyroid Carcinoma, PLoS ONE 10(7): e0132403.Oncotarget, vol. 7, No. 11.
Minna et al., miR-451a is underexpressed and targets AKT/mTOR pathway in papillary thyroid carcinoma, Oncotarget, vol. 7, No. 11, 12731-12747, Feb. 8, 2016.
Mueller et al., MicroRNAs and Their Impact on Radiotherapy for Cancer, Radiation Research 185, 668-677 (2016).
Riese et al., Epiregulin: Roles in normal physiology and cancer, Seminars in Cell & Developmental Biology 28 (2014) 49-56.
Riquelme et al., The Gene Expression Status of the PI3K/AKT/mTOR Pathway in Gastric Cancer Tissues and Cell Lines, Pathol Oncol Res. Oct. 2016 ; 22(4): 797-805.
Rodel et al., Spontaneous and Radiation-Induced Apoptosis in Colorectal Carcinoma Cells With Different Intrinsic Radiosensitivities: Survivin as a Radioresistance Factor, Int. J. Radiation Oncology Biol. Phys., vol. 55, No. 5, pp. 1341-1347, 2003.
Schetter et al., MicroRNA Expression Profiles Associated With Prognosis and Therapeutic Outcome in Colon Adenocarcinoma, JAMA. 2008;299(4):425-436.
Sestini et al., Circulating microRNA signature as liquid-biopsy to monitor lung cancer in low-dose computed tomography screening Oncotarget, vol. 6, No. 32, 32868-32877, Oct. 6, 2015.
Tian et al., MicroRNA miR-451 downregulates the PI3K/AKT pathway through CAB39 in human glioma, International Journal of Oncology 40: 1105-1112, 2012.

(Continued)

*Primary Examiner* — Kimberly Chong
(74) *Attorney, Agent, or Firm* — Steven R. Eck

(57) ABSTRACT

Disclosed are methods of treating colorectal cancer that involve administering a composition comprising an effective amount of miR-451a to cells in the colorectal cancer and further treating the colorectal cancer cells with ionizing radiation. Also disclosed are methods of predicting whether a colorectal cancer in a subject will respond to ionizing radiation. These methods involve measuring the RNA expression of miR-451a, miR-1322, miR-133-3p, miR-1, miR-205-5p, miR-4521, CAB39, EMSY, or MEX3C in the sample and measuring the RNA expression of the same marker in a control.

15 Claims, 11 Drawing Sheets
Specification includes a Sequence Listing.

(56) References Cited

OTHER PUBLICATIONS

Tian et al., Upregulation of microrna-451 increases the sensitivity of A549 cells to radiotherapy through enhancement of apoptosis, Thoracic Cancer 7 (2016) 226-231.

Tsikitis et al., Differential expression of microRNA-320a, -145, and -192 along the continuum of normal mucosa to high-grade dysplastic adenomas of the colorectum, The American Journal of Surgery (2014) 207, 717-722.

Tsikitis et al., MicroRNA Signatures of Colonic Polyps on Screening and Histology, Cancer Prev Res; 9(12); 942-9, 2016.

Vychytilova-Faltejscova et al., Serum-based microRNA signatures in early diagnosis and prognosis prediction of colon cancer, Carcinogenesis, 2016, vol. 37, No. 10, 941-950.

Anand et al., MicroRNA regulation of endothelial TREX1 reprograms the tumour microenvironment, Nature Communications, (2016), vol. 7, 13597, pp. 1-10.

Anand et al., Emerging Role of Micro-RNAs in the Regulation of Angiogenesis, Genes & Cancer 2(12) 1134-1138.

Anand et al., MicroRNA-mediated regulation of the angiogenic switch, Current Opinion in Hematology 2011, 18:171-176.

Liu et al., miR-451a Inhibited Cell Proliferation and Enhanced Tamoxifen Sensitive in Breast Cancer via Macrophage Migration Inhibitory Factor, BioMed Research International, vol. 2015, Article ID 207684, 12 pages.

2) Zhang et al., MiR-451 increases radiosensitivity of nasopharyngeal carcinoma cells by targeting ras-related protein 14 (RAB14), Tumor Biol 35,12593-12599 (2014).

Acharya et al., Serum microRNAs are early indicators of survival after radiation-induced hematopoietic injury, Science Translational Medicine, May 13, 2015 vol. 7 Issue 287 287ra69.

Amirkhah et al., MicroRNA—mRNA Interactions in Colorectal Cancer and Their Role in Tumor Progression, Genes, Chromosomes & Cancer 54:129-141 (2015).

\* cited by examiner

| miR identifiers | | 6h | |
|---|---|---|---|
| miR | Probeset ID | HCT-116 | SW480 |
| hsa-miR-451a | MIMAT0001631_st | 5.06 | 2.26 |
| hsa-miR-1322 | MIMAT0005953_st | 2.03 | 2.03 |
| hsa-miR-4521 | MIMAT0019058_st | -5.18 | -13.04 |
| hsa-miR-205-5p | MIMAT0000266_st | -6.46 | -3.08 |

| miR identifiers | | 48h | |
|---|---|---|---|
| miR | Probeset ID | HCT-116 | SW480 |
| hsa-miR-133a-3p | MIMAT0000427_st | 2.84 | 3.01 |
| hsa-miR-1 | MIMAT0000416_st | 7.10 | 2.24 |
| hsa-miR-205-5p | MIMAT0000266_st | -37.75 | -2.33 |
| hsa-miR-3911 | MIMAT0018185_st | 2.41 | -2.34 |
| hsa-miR-16-1-3p | MIMAT0004489_st | -2.49 | -2.55 |
| hsa-miR-181c-3p | MIMAT0004559_st | -2.50 | -5.45 |

SEQUENCE LISTING

<160> NUMBER OF SEQ ID NOS: 9

<210> SEQ ID NO 1
<211> LENGTH: 22
<212> TYPE: RNA
<213> ORGANISM: Homo sapiens

<400> SEQUENCE: 1
aaaccguuac cauuacugag uu                                              22

<210> SEQ ID NO 2
<211> LENGTH: 19
<212> TYPE: RNA
<213> ORGANISM: Homo sapiens

<400> SEQUENCE: 2

-continued

| | |
|---|---|
| gaugaugcug cugaugcug | 19 |

<210> SEQ ID NO 3
<211> LENGTH: 22
<212> TYPE: RNA
<213> ORGANISM: Homo sapiens

<400> SEQUENCE: 3

| | |
|---|---|
| uuuggucccc uucaaccagc ug | 22 |

<210> SEQ ID NO 4
<211> LENGTH: 71
<212> TYPE: RNA
<213> ORGANISM: Homo sapiens

<400> SEQUENCE: 4

| | |
|---|---|
| ugggaaacau acuucuuuau augcccauau ggaccugcua agcuauggaa uguaaagaag | 60 |
| uauguaucuc a | 71 |

<210> SEQ ID NO 5
<211> LENGTH: 22
<212> TYPE: RNA
<213> ORGANISM: Homo sapiens

<400> SEQUENCE: 5

| | |
|---|---|
| uccuucauuc caccggaguc ug | 22 |

<210> SEQ ID NO 6
<211> LENGTH: 22
<212> TYPE: RNA
<213> ORGANISM: Homo sapiens

<400> SEQUENCE: 6

| | |
|---|---|
| gcuaaggaag uccugugcuc ag | 22 |

<210> SEQ ID NO 7
<211> LENGTH: 3846
<212> TYPE: DNA
<213> ORGANISM: Homo sapiens

<400> SEQUENCE: 7

| | |
|---|---|
| gcagtgcgca cgtcaaagcc gggctcgggc cgcaagcggg gcgaggggtt cggggagcgg | 60 |
| cgcggcctgg gagacacaga gccttcaggc gccggggcgg gggcacaggc gaagactaag | 120 |
| gcggcgccgg gccccacagc agcagccgca gcccaagcga gcgcagcagc gcggcggcag | 180 |
| ccgcgggagc ccctgggcag ccgtccgccc gcgcagccgc cgccgccgcg ggagcccgtc | 240 |
| gccgggagca ggagcgggcg gaagacaacg gaggggccga gcgtccgagc cactccgcgg | 300 |
| ggaccgaacg agcagcccga agcggcggcg gccgaggacg gggacagcga cgacgcggag | 360 |
| gcagagaagg gaacgcccgg cccagccccg tagcacaggc ggagtgcagc ggaggccccct | 420 |
| gccgctgccg tcatgccgtt cccgtttggg aagtctcaca aatctccagc agacattgtg | 480 |
| aagaatctga aggagagcat ggctgttctg gaaaagcaag acatttctga taaaaagca | 540 |
| gaaaaggcta cagaagaagt ttccaaaaat ctggttgcca tgaaagaaat tctgtatggc | 600 |
| acaaatgaaa aagagcctca gacagaagca gtagctcaac ttgctcaaga actctataat | 660 |
| agtgggctcc ttagcaccct ggtagctgat ttacagctca ttgactttga gggcaaaaaa | 720 |
| gacgtggctc aaattttcaa caatattctc agaagacaaa ttggtacgag aactcctact | 780 |

```
gttgaataca tctgcaccca acagaatatt ttgttcatgt tattgaaagg gtatgaatct        840
ccagaaatag ctctaaattg tggaataatg ttaagagaat gcatcagaca tgaaccactt        900
gcaaaaatca ttttgtggtc ggaacagttt tatgatttct tcagatatgt cgaaatgtca        960
acatttgaca tagcttcaga tgcatttgcc acattcaagg atttacttac aagacataaa       1020
ttgctcagtg cagaattttt ggaacagcat tatgatagat ttttcagtga atatgagaag       1080
ttacttcatt cagaaaatta tgtgacaaaa agacagtcac tgaagcttct cggtgaacta       1140
ctactagata gacacaactt cacaattatg acaaaataca tcagtaaacc tgagaacctc       1200
aaattaatga tgaacctgct gcgagacaaa agtcgcaaca tccagtttga ggcctttcac       1260 gttttttaagg tgtttgtagc caatcctaac aagacgcagc ccatcctaga catcctcctc      1320
aagaaccagg ccaaactcat agagttcctc agcaagtttc agaacgacag gacgaaggat      1380
gagcagttta cgacgagaa gacctattta gttaaacaga tcagggattt gaagagacca        1440
gctcagcaag aagcttaatc tccaataaac atctatgtta aatccaaatt cagcatttgc      1500
tgttagctat tcagcatcag gcactcttat tgattcatga ggaacattac tgctaatctg      1560
ctgttaagtg aacggttttt cattttaccc ttttgttttt cagtccaggt tggagatcgt      1620
agctgctgct gcttgcacac tagggcacat gtgggctttc tcttgatctt tgtgtcattt      1680
cagaattcaa agactgtgct acgggagttc tgaacatggc tgggttcatg aaggcaaatg      1740 tatgatgag agtgtggttt aggaaagagg gcactgatat cagattagac ctatgtgttt        1800
gcacccatct tgttggcga tctgagtgca gtgtggcaag tgcacacctg gcatccctgc        1860
gtcagatcgc gcaccttcag gtcgcgcacc ttcgctgaag gaagatgacg cagagcttta      1920
tctgaaatca gagggagct atccaaaatg ggagtttggg ggcagctaaa gttgacatgc        1980
gaataaattg atactgaaac ttagcaactt cttaaaagtg taaagaagcc tcataagatc      2040
ataaggaaaa tgtatatatg cttttcacag ctttctagaa ttttttgaca tttgattttc      2100
ttgagacttg taaacctgga tatgttgaag ggtatttgtt aattttactt ttcaaagata      2160
cttaaaaaca gtagagctag caatgacacc ttgcatttca tttcaacact gcttcaaggt      2220
ttcttttgta tataattctt agaatgctca tttctttaa atggtttaat ttgtacagca       2280
gaggaatgtt attgtagtag tatgtaacta ttacctaata ctgagttttt gcaaaaaaca      2340
atgaatgctc atatgtaatt gaaatacttc agatacatg aaaatgctga tttaacattt       2400
aagtatcaca gcattaaaag aaaaagaaag taaaccagtc ctttgtattc agttacctaa      2460
tggggtgcca tcaataagct gcgatacagc cctggagctc agtcagccac accttcctgc      2520
atcctattgg ccttattcat tttaaatgag ttaatgaatc tgccagatct gtgaatgata      2580
gagattatgc taaattaatg ctgattcttt gtgtgtgtgg gaaatctctg tagagcacct      2640
tttctttctt agactaagta acccagtaca atagttgtga actgaataat taaaactttg      2700
gcttctctta ggaaaagacg acttcctagt cataggtgtc ctatggggaa atttatttt       2760 tttaatgtcc tgttccttaa tgctgcaaat tatcagtatt tataaagtaa ctgatttgc       2820 accactttt tgttactgtg accacggcag aacaatgtct tctagactat atctatgtaa       2880
agttattaga atggtatctg ttcattttag tgatatgaag atcacaacta acaactgaca      2940
aatcagagtt tgccagttca aattcagcat ggctgcagct gattaagaaa ttgatatgat      3000
tattctttgc tagcctctct tactaatgga attatatact ggccagtaaa atgggcctcc      3060
caattgctgt tcagcaggt tttaaacctt caggaacacc agttaggaaa atagctccag       3120
aaaatataga tatatttat ttttattaaa atggcagtct acatcataat tggcatttct       3180
```

| | | |
|---|---|---|
| caagactgtc tttaccagaa tctgtgtgaa ataaggcaat ctagtctcct tgaaaaaaaa | 3240 |
| atctcttgga tgtttaggaa ggaagacttg gccgtgatgt ggtgtcctgg cttttgtggtg | 3300 |
| tagtgctgtg tgtatggagt tagtgtaaaa acatggatta caccaagtgg aagaaacgtc | 3360 |
| ttcttgccaa gctcattctt agaacttaca catctagaac agcttccact ttggcagtga | 3420 |
| ggtcgtagcc ttttaggtgg aagaagtgag ggtgcagcgt gtcagacaca acattcatgt | 3480 |
| tactcttaca ttggaatctg aaggtagttc agacttcgtg ggttttgttt ttaagcaaaa | 3540 |
| caatgtgaaa acatttaagt ttgaaatgtt gcatttgaag ttatgatcat ttaatatatt | 3600 |
| catattacca agactattat actggaagtg gttttttgtgt tataaaggtt taattttaca | 3660 |
| taaggcagtt acttaatgtg attttttaacc cttaaaaaag tggagatgta tacatttgtt | 3720 |
| aacaatgcca tgaaagcatt ttcttttctcc taaggaaaag tgaatttctt atcagaatat | 3780 |
| ctggctggcc ctgtaatttta aattaaaata aaatttttgga gaaacagcaa aaaaaaaaa | 3840 |
| aaaaaa | 3846 |

<210> SEQ ID NO 8
<211> LENGTH: 6916
<212> TYPE: DNA
<213> ORGANISM: Homo sapiens

<400> SEQUENCE: 8

| | | |
|---|---|---|
| gtcgccatct tgccccttca gaggcaccgc aaacaaaccc aattcctggt gtcccctagt | 60 |
| cttggcggag gagcctttta gatgagcccc gaaaggccgg gcagggagga caagctcttt | 120 |
| ggggctacca aacagaagca gcaatgcctg ttgtgtggcc aacccttctg gatctcagca | 180 |
| gggatgaatg caaagaatt cttcgaaaat tggaattgga ggcatatgct ggagttatca | 240 |
| gtgcacttcg ggcacagggg gatctcacca aggaaaagaa agatcttctt ggagaactat | 300 |
| caaaagttct tagcatctca acagaacgcc accgtgctga agttcggaga gcagtaaacg | 360 |
| atgaacggtt aacaacaatt gcacataaaa tgaatttatc cttatatttg ggtgaaagac | 420 |
| caagttacag tatgtctgga cctaatagct cttcagaatg gtccattgaa ggtcgtcgat | 480 |
| tggtaccact gatgccccgg ctcgttcccc aaaccgcctt tactgtaaca gctaatgctg | 540 |
| ttgctaatgc agctatccag cataatgcat ctcttccagt gcctgcagaa acaggaagca | 600 |
| aggaagtagt ggtttgctat tcctacacaa gtaccacgtc aaccccaacc tctacccctg | 660 |
| ttccaagtgg cagcatagca acggttaagt ctccaagacc tgccagtcct gcctccaatg | 720 |
| tagttgtctt gccaagtgga agtactgttt atgtcaaaag tgtaagctgt tcagatgaag | 780 |
| atgaaaaacc cagaaaacga aggcgaacaa actcttccag ctcctctcct gttgttctaa | 840 |
| aggaagttcc aaaggccgtt gttccagtct caaagacgat cactgtgcct gtgagtggta | 900 |
| gtcccaagat gagcaacatc atgcagagca ttgccaactc cttaccaccc cacatgtctc | 960 |
| ctgtaaaaat aaccttcact aaaccatcaa cacagacaac aaaacacaaca acacagaagg | 1020 |
| ttattatagt caccacatca ccaagctcaa ccttcgtgcc caacattctc tccaaatccc | 1080 |
| ataactatgc agcagtcact aagcttgtac caacgtcagt cattgcttct acaacccaga | 1140 |
| agccaccagt tgttataact gcttcacagt cctctctggt cagtaatagc agcagtggca | 1200 |
| gcagcagttc tacaccatca cctattccta atacagttgc agtaacagct gtggtgtcct | 1260 |
| ctacaccatc tgtggtcatg tcaacagtag cacaaggtgt atctacatca gcaatcaaaa | 1320 |
| tggcatcaac cagacttcct tcccccaaaa gcttagtgag tgccccaact cagattcttg | 1380 |

```
cacagttccc taaacaacat caacagtctc ctaagcagca gttatatcaa gtgcaacagc      1440
agacacagca acaagtggcc cagccttctc cagtatctca tcagcaacag cctcagcagt      1500
ctcctttgcc acctggtatt aaacctacca tccaaatcaa acaggagtca ggtgttaaaa      1560
tcatcacaca acaggttcaa ccaagtaaaa tcttacccaa accagtgaca gcaactctac      1620
ccaccagtag caattcccct attatggtgg ttagcagtaa tggtgcaatt atgacaacta      1680
aactggtaac cactcctact ggcacacaag caacctatac ccggccaaca gtgagcccat      1740
ccattggtcg gatggctgca acccctggag ctgcaaccta tgtgaaaact acgagtggta      1800
gcatcattac agtagtaccc aaatcattag ctaccttggg gggcaagata attagcagta      1860
atatagtttc tggaacgact accaaaatca ctacaatccc aatgacttcc aagcccaacg      1920
tgattgttgt acaaaagact acaggaaaag gaacgaccat tcaaggcctc ccgggcaaaa      1980
atgttgtcac aacgttgcta aatgctggag gagaaaagac tattcagaca gtgccaacag      2040
gagcaaagcc agctatcctt actgctacaa gacccatcac caaaatgatt gtaacgcagc      2100
caaaaggaat aggttctaca gttcaaccag cagctaaaat catcccaaca aaaattgttt      2160
atgggcagca agggaaaacg caggttctta ttaaacccaa accagtgact tttcaagcga      2220
cagttgttag tgaacaaaca agacagctag taacagaaac attacagcaa gcatccaggg      2280
tagcagaggc tggtaattca tctattcagg aaggaaaaga agaaccacag aattatacag      2340
atagtagttc ctcttctaca gagtcctccc agagttccca agattcccag cctgtagttc      2400
atgtaattgc ttcccggcgt caggattggt cagaacatga gattgcaatg gagactagcc      2460
ctaccataat ttatcaggat gtatccagtg aatcacaatc agctacttca acaatcaaag      2520
ctctgttaga actccaacag acaacagtaa aggaaaaatt ggaatctaaa ccaagacaac      2580
ccactattga cctgagtcaa atggcagtgc ctattcagat gacccaggaa agagacatt       2640 ctcctgagag tccatcaatt gctgtggtag agtcagaact agtagctgaa tacatcacta      2700
ctgaacgcac tgatgagggg acagaggttg cttttcccct tctagtcagc catcgctccc      2760
agccccaaca gccttcccag ccccagcgga ccctgctcca gcatgtggct cagtcacaga      2820
ccgcaacaca gacttcggtg gtggtgaagt ccatcccagc atcttccct ggagcaatca       2880 cccacattat gcagcaggca ttaagcagtc acactgcttt taccaaacac agcgaggaac      2940
ttggaactga ggagggcgag gttgaagaga tggacacttt agaccctcag acaggtctgt      3000
tttaccgatc tgccctgact cagtcacagt cagctaaaca gcagaaactt agccagcccc      3060
cgctggaaca gactcagctg caagtgaaaa ctctgcagtg cttccagact aaacagaagc      3120
agaccatcca cctgcaggca gaccagctcc agcacaaact cccgcaaatg ccccagcttt      3180
ccatcaggca tcaaaaactc acccctctcc agcaagaaca agcacagccc aagccagatg      3240
tacagcacac acagcatccc atggtggcca agacaggca gcttcctacc ttaatggcac       3300 agccccgca aactgtagta caggtgcttg cagtgaaaac cacgcagcag ctccctaaac       3360
tgcagcaggc tccgaaccaa ccaaaaatct acgtgcaacc caaaccccc cagagccaaa       3420 tgtcgctccc agcttcttca gagaaacaga cggcaagcca ggtggagcag ccaattataa      3480
cccaaggatc ctctgttaca aagataactt ttgaggggcg ccagcctccc acagttacaa      3540
agataactgg tggcagttct gtgcctaagc tgacatcacc agttacaagc atatctccca      3600
ttcaggcctc tgagaagaca gcagtgtctg acatttttgaa aatgtctttg atggaagctc      3660
agattgatac aaatgtagaa catatgatag tggatccccc aaagaaggct cttgccacta      3720
gcatgctcac tggtgaagca ggatcattac cctccaccca catggtggtg gcagggatgg      3780
```

```
cgaattccac tccccagcaa cagaaatgta gagagtcctg ttcgagtcca tccactgttg    3840
gctcttccct aacgacaagg aaaattgatc caccagcagt gcctgcgaca ggccagttca    3900
tgcgtattca gaatgtaggc caaaagaaag ctgaagagag tccagcagaa attatcatcc    3960
aggctattcc tcagtatgct attccttgtc actccagctc caatgtggtg gtggagccca    4020
gtgggcttct tgagctaaac aacttcacta gtcaacagct ggatgatgag gagacagcaa    4080
tggagcagga catagacagt agcacggagg atggaactga acccagccct tctcagagct    4140
ctgctgaacg gtcctagtgt ttggacacaa tagtgcactt taaaacctgc ttggttacca    4200
agtgtccagg gaaacccttg tattttgatg actaaaaaga gcactttgcc cgtacttagg    4260
ctgtggaccc taaaacagca gtgtttcaac aagatgttgc tgcaggagca gcttttttaaa    4320 acaagataaa actcacaggg gaatgtactt ttttaaaaaa aaatgaaaaa gaaaaaaaaa    4380
gctgcacatt tacagtgact taagacctgg tcttctttct ctgttggatc atggccggtg    4440
aaacagtttt gtcttgcagt ggaaagagac ttcctgtgaa tgtttctcaa ctggtttcta    4500
ctgagcaaaa taccatctaa aaggagaatg tgaatagttg tattttgaaa tgatgtgtca    4560
ggaaaagttt tttaaaaact tgtatgtttt tgcaaatccc tggaagtgtt gaattggtta    4620
aaattttaca ttttctcagt tcataattag tttataaaca cctagaataa tactggcatt    4680
aaagaatcct tgttggatgg tagaaatcag atccctaacc agtgggaggt acttttggg    4740 tggcttgtgc attcttatca gttgtgtgct aatttattgt attgttcctt tgtgctctaa    4800
gcagcacact tgccttctat ttatttaagt gtaaacattt caaagcaggc cgtactcctt    4860
ctgacaaatt tcttgtaaac caggattgcc tacgctttcc actgtcgtcg tctccccact    4920
ttccctcttc ctttaagaaa acttactaaa aaatgtttca ttgcgaagca gaggaaaaga    4980
aacgttttca gacctaaagg aaatgtttgg tcatgttaag aaaacaaatt attcattcat    5040
atgatgcttt cttaacgttg aaattgcaca ttcacattgg actgagactt tgaaaataac    5100
ttttacatac ttttgtttaa gccccttttga aatgtataaa aagttcattt acagttctaa    5160
atgtaatgtt tttaagcctt ctatcttttt aggacacagt ttgtttaagc aatatgtttt    5220
ggtcttgtga tcactgtctg tcacaagtag agtgaaaggg gtaaggggt gggagggtaa    5280 gagttttgac aagttgtggc aaaggaaact atacttttca ttttttaaaaa tgtaaataga    5340 aaagttttta acggttttat atagatttca ctataaataa gcattttaag actgacaaat    5400
gttgaactgt acatacattt atcagcataa ctgcccagtt ttttttggtgc tgaagtactg    5460 taagtagaat tcatcaacgg tctcctaatt tttgcatcta catctggggg gaaaaagctg    5520
tgatactata gttaataaat tcccactaga gtgacactga agatttaaac acaagcattc    5580
ataagatgcg ctgatctctg gtggttgtca ctagttctgc taggtgataa tgatttaccc    5640
atagatggag ctgttggata ttattttatt gtacaaattc atgtttaaaa aactttgtga    5700
ctgtttctag ttaagtaatt ttttaacctt tctgggtca tagacttctt tggtaaaacta    5760 tgaactctca ccaaaaagat acacatgcaa catgttaaat acatgttaga ctttgcatac    5820
aattttaggg gctcatgggc ctctaagcct atccatgtat tccaggttaa gccctctgtt    5880
atgatcaatc cattacttac agattaagtt tttataaaat aaagtatctt ttaaatattc    5940
atggatcaag taacaagagc aaacttgaat aaagttatgt tctacatatt ttggcagcat    6000
agcatacctg tgtcccttga gaatttagcc ttcatatgtt tctgcaattg gaatggcaaa    6060
taaaagtgct atcatctaca tttttttaaa gaattacaaa tattaagaaa ttatcaagtg    6120
```

```
aaatttaaaa ttttttcttt aaaggtgtta attccaaata gagcatgcat tcatttattt    6180
attcaacaaa tattaattga gcatcttctg tatgacaagt agtattctgt gcactgggga    6240
taccatagtg aacaaacagg aaatcctatc cttatgaagt ttataaacag ggcttcctgc    6300
tcatgaaatg gatacaagga atgaagacag gagaaaataa gaacaatact taggtttttt    6360
tataaagtgg atagatgatg atgccatata tggattttca gacatccctt tactgaaagt    6420
cttagcatta tatctattag tattccacat ttaagtacat aatttaaaag taatttaaag    6480
tcatctcttt gaaggatatt aacaaattac aatgcaaatg ctacagaatt tttagaatcc    6540
taacaactat taggcagtga taagaaaaat ccatttggct taaagtaaac tttaataagt    6600
gcctagtatt gcagatgcag tttatggtga acttagagga ttaaaaacca aaggggctt    6660
cattgagata ttcacatgcc ataaactctc ccatttaaag tataccgttt aatggtttta    6720
gtatatccac agagttgggc aagccattac cacaatcaat ttgagaacat tttcattaat    6780
cacaaaagaa atcctgaaat gaaaccacca ccaccatcgc tccagccctg ggtggccact    6840
cctctacttt ctgcctctta tggatgtgcc ataagaaatg tggacatttc atataaatga    6900
gattatataa aaaaaa                                                    6916

<210> SEQ ID NO 9
<211> LENGTH: 1980
<212> TYPE: DNA
<213> ORGANISM: Homo sapiens

<400> SEQUENCE: 9
atgcccagcg gcagctccgc ggccctggcc ctggcggcgg ccccggcccc cctgccgcag      60
ccgcccccgc cgccgccgcc gccaccgccg cctctgccgc cgccctcggg cggcccggag     120
ctcgaggggg acgggctcct gctgagggag cgcttggccg cgctaggcct cgacgacccc     180
agcccggcgg agcccggcgc cccggcgctt cgggccccgg cagcggcggc gcagggccag     240
gccccggcgg cggcggagct gtctccagag gagcgggctc cgcccggccg gcccggggcc     300
ccggaggcgg ccgagctgga gctggaagag gacgaggagg agggggagga agcggagctg     360
gacggagacc tgctggagga ggaggagctg gaggaagcag aggaggagga ccggtcgtcg     420
ctgctgctgc tgtcgccgcc cgcggccacc gcctctcaga cccagcagat cccaggcggg     480
tccctggggt ctgtgctgct gccagccgcc aggttcgatg cccggaggc ggcggccgcg     540
gcggcggcgg cggggtgct gtacggaggg gacgatgccc agggcatgat ggcggcgatg     600
ctgtcccacg cctacggccc cggcggttgt ggggcggcgg cggccgccct gaacggggag     660
caggcggccc tgctccggag aaagagcgtc aacaccaccg agtgcgtccc ggtgcccagc     720
tccgagcacg tcgccgagat cgtcggccgc cagggttgta aaattaaagc actgagagcc     780
aagacaaaca cgtatatcaa gactcctgtt cgtggtgaag agcccatttt tgttgtcact     840
ggaaggaaag aagatgttgc catggccaaa agagagatcc tctcagctgc agagcacttc     900
tccatgattc gtgcatctcg aaacaaaaat gggcctgccc tgggaggatt atcatgtagt     960
cctaatctgc ccggtcaaac caccgtccaa gtcagggtcc cttatcgtgt ggtaggatta    1020
gtggttggac ccaaaggagc aactattaaa agaattcagc agcagaccca cacctacata    1080
gtaactccga gcagagataa ggaacctgtc tttgaagtga cagggatgcc tgaaaatgtt    1140
gaccgagcac gggaagaaat agaaatgcat attgccatgc gtacaggaaa ctatatagag    1200
ctcaatgaag agaatgattt ccattacaat ggtaccgatg taagctttga aggtggcact    1260
cttggctctg cgtggctctc ctccaatcct gttcctccta gccgcgcaag aatgatatcc    1320
```

```
aattatcgaa atgatagttc cagttctcta ggaagtggct ctacagattc ctactttgga    1380
agcaataggc tggctgactt tagtccaaca agcccattta gcacaggaaa cttctggttt    1440
ggagatacac taccatctgt aggctcagaa gacctagcag ttgactctcc tgcctttgac    1500
tctttaccaa catctgctca aactatctgg actccatttg aaccagttaa cccactctct    1560
ggctttggga gtgatccttc tggtaacatg aagactcagc gcagaggaag tcagccatct    1620
actcctcgtc tgtctcctac atttcctgag agcatagaac atccacttgc tcggagggtt    1680
aggagcgacc cacctagtac aggcaaccat gttggccttc caatatatat ccctgctttt    1740
tctaatggta ccaatagtta ctcctcttcc aatggtggtt ccacctctag ctcacctcca    1800
gaatcaagac gaaagcacga ctgtgtgatt tgctttgaga atgaggttat tgctgcccta    1860
gttccatgtg gccacaacct cttctgcatg gaatgtgcca acaagatctg tgaaaagaga    1920
acgccatcat gtccagtttg ccagacagct gttactcagg caatccaaat tcactcttaa    1980
```

COMPOSITIONS AND METHODS USED IN DIAGNOSING AND TREATING COLORECTAL CANCER

PRIORITY

This application claim priority to U.S. Provisional Patent Application No. 62/443,129, filed 6 Jan. 2017, the entirety of which is incorporated herein by reference.

REFERENCE TO SEQUENCE LISTING

A computer readable text file entitled "2359-2_ST25.txt" created on or about Jan. 3, 2018, with a file size of 18 KB, contains the sequence listing for this application and is incorporated by reference herein in its entirety.

FIELD OF THE INVENTION

Generally, the field involves biotherapeutics and diagnostic tests. More specifically the field involves RNA-based biotherapeutics and diagnostic tests.

BACKGROUND OF THE INVENTION

In 2016, an estimated 134,000 patients will be diagnosed with colorectal cancer. Among the rectal cancer subset, patients with locally advanced disease, staged as T3-T4 and or node positive, receive neoadjuvant chemoradiation therapy (CRT) and subsequent surgery (Nelson H et al, J Nat Cancer Inst 93, 583 (2001) and Kalyan A et al, Gastroenterology Report 2016; both of which are incorporated by reference herein). While 10-25% of patients have complete response to CRT, the remaining patients undergo extensive tumor excision that leads to considerable quality of life issues (Maas M et al, Lancet Oncol 11, 835 (2010); incorporated by reference herein). Moreover, response to CRT is an independent predictor of overall survival in colorectal cancer (Agarwal A et al, Cancer 119, 4231 (2013); incorporated by reference herein) highlighting the importance of improving CRT response rates. It is known that several tumor intrinsic factors govern responses to CRT including specific gene expression programs with distinct significance ascribed to microRNAs (miRs) (Rodel C et al, Int J Rad Oncol Biol Phys 55, 1341 (2003) and Eschrich S A et al, Int J Rad Oncol Biol Phys 75, 489 (2009); both of which are incorporated by reference herein). miR-processing machinery is frequently mutated in colorectal cancers, and miRs have been implicated in several pathological processes associated with colorectal cancer progression including cancer stemness and epithelial-to-mesenchymal transition (EMT) (Amirkhah R et al, Genes Chrom Cancer 54, 129 (2015) and Schetter A J et al, J Am Med Assoc 299, 425 (2008); both of which are incorporated by reference herein). Emerging evidence suggests that microRNAs (miRs) modulate gene expression programs in response to radiation and confer variable sensitivity and efficacy to modern high dose ionizing radiation therapy (Mueller A K et al, Rad Res 185, 668 (2016); incorporated by reference herein).

SUMMARY OF THE INVENTION

It is disclosed herein that miR-451a is a tumor suppressor miRNA in colorectal adenocarcinoma the presence of which correlates with greater efficacy of radiation treatment. Through gain and loss-of-function studies, it is disclosed that miR-451a is a negative regulator of proliferation in colorectal cancer (CRC) and likely mediates its effects by targeting CAB39 and EMSY.

Disclosed herein are methods of treating subjects with colorectal cancer. These methods involve administering a pharmaceutical composition including an effective amount of miR-451a to colorectal cancer cells within the subject such that the miR-451a is present and/or expressed within the colorectal cancer cells and administering a dose of at least 1 Gy of ionizing radiation to the colorectal cancer cells thereby treating the colorectal cancer. The method can further involve administering a dose of 5-fluorouracil to the subject. The source of the ionizing radiation can be any effective form of ionizing radiation including an alpha-emitter, a beta emitter or a gamma emitter.

Also disclosed herein are methods of predicting whether a colorectal tumor from a subject will be sensitive to or resistant to ionizing radiation. The method involves receiving a sample comprising colorectal cancer cells from the colorectal tumor, measuring the RNA expression of a first biomarker selected from miR-451a, miR-1322, miR-133-3p, miR-1, miR-205-5p, miR-4521, CAB39, EMSY, or MEX3C in the sample, and measuring the RNA expression of the first biomarker in a non-irradiated control cell. Expression of miR-451a, miR-1322, miR-133-3p, or miR-1 in the sample that is greater than the control is an indication that the colorectal tumor will be sensitive to ionizing radiation and expression of miR-205-5p, miR-4521, CAB39, EMSY, or MEX3C in the sample that is greater than the control is an indication that the tumor will be resistant to ionizing radiation. The method can further involve, upon an indication that the colorectal cancer will be resistant to ionizing radiation, predicting that the probability of survival of the subject after 40 months will be less than 60%.

DETAILED DESCRIPTION OF THE INVENTION

Figures 1A, 1B:
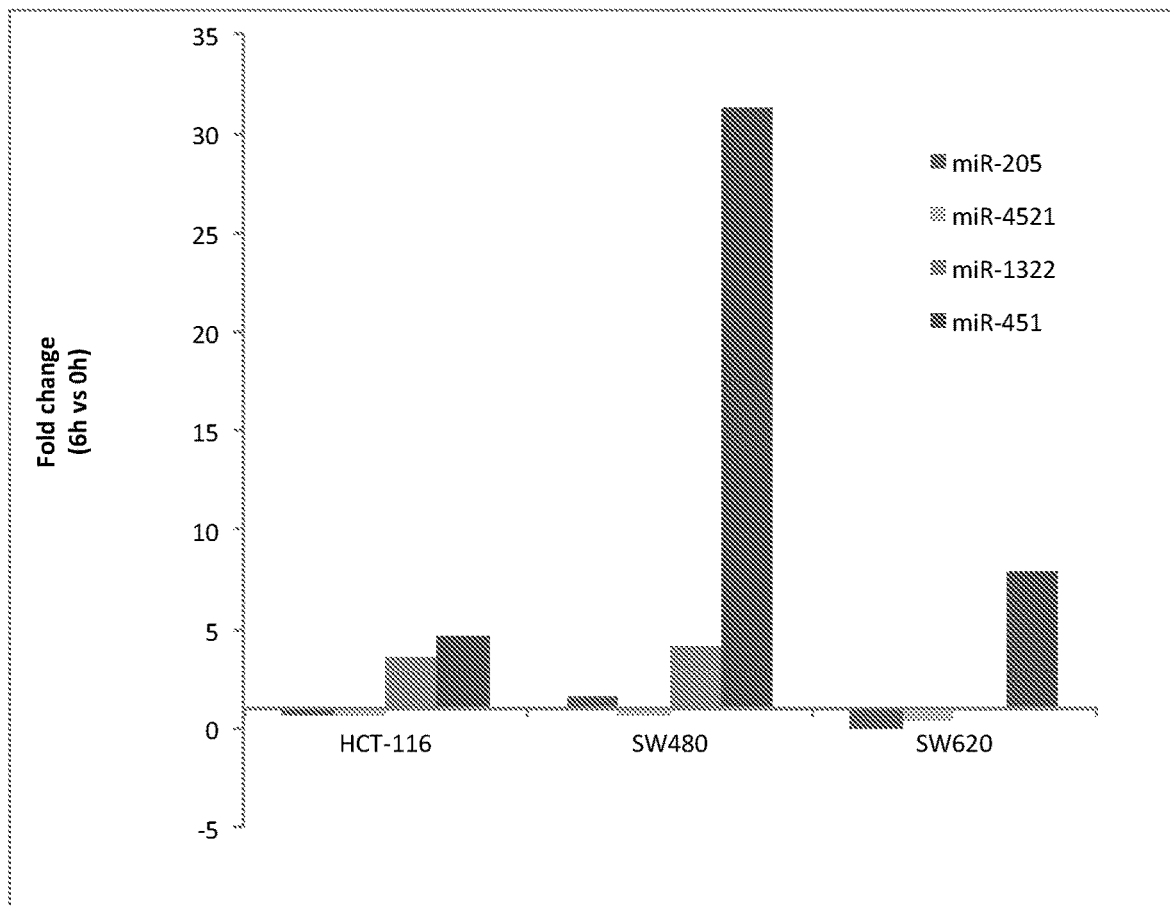
FIG. 1A is a schematic of the design of the screen for miRs induced by radiation and a table of miRs with more than 2 fold change from the Affymetrix microRNA array v4.0® across both tumor types.
FIG. 1B is a graph showing the levels of the two most upregulated and downregulated miRs 6 h post 2 Gy radiation validated by qRT-PCR using specific Taqman probes for each microRNA. Mean fold change after normalization to a housekeeping RNA, RNU48, is depicted.

Provided is a method of sensitizing colorectal cancer cells in a subject to ionizing radiation, the method comprising administering to a subject in need thereof an effective amount of miR-451a (SEQ ID NO: 1).

Provided is also a method of inducing colorectal cancer cell death or colorectal cancer cell terminal differentiation in a subject, the method comprising:
a) administering to a subject in need thereof an effective amount of miR-451a (SEQ ID NO: 1); and
b) exposing the colorectal cancer cells within the subject in need thereof to at least one dose of ionizing radiation.

Also provided is a method of treating a subject with colorectal cancer in a subject, the method comprising:
administering a pharmaceutical composition comprising an effective amount of miR-451a (SEQ ID NO: 1) to colorectal cancer cells within the subject in need thereof such that the miR-451a is present and/or expressed within the colorectal cancer cells; and
administering to the colorectal cancer cells within the subject in need thereof a dose of at least 1 gray (Gy) of ionizing radiation.

Further provided is a method of reducing the growth, proliferation, or survival of colorectal cancer cells in a subject, the method comprising:
a) administering to a subject in need thereof an effective amount of miR-451a (SEQ ID NO: 1); and
b) exposing the colorectal cancer cells within the subject in need thereof to at least one dose of ionizing radiation.

Also provided is a kit for sensitizing colorectal cancer cells in a subject to radiation, the kit comprising a therapeutically effective amount of miR-451a (SEQ ID NO: 1) and instructions for using the miR-451a to sensitize colorectal cancer cells in a subject to radiation.

In some embodiments, the dose of at least 1 Gy of ionizing radiation is selected from the group of 1 Gy, 2 Gy, 3 Gy, 4 Gy, 5 Gy, 6 Gy, 7 Gy, 8, Gy, 9 Gy, and 10 Gy per dose. In other embodiments, the dose of at least 1 Gy of ionizing radiation is selected from the group of 1 Gy, 2 Gy, 3 Gy, 4 Gy, 5 Gy, and 6 Gy per dose. In other embodiments, the ionizing radiation is dosed at from about 1 Gy to about 3 Gy per dose. In other embodiments, the ionizing radiation can be administered at 2 Gy per dose for a total cumulative dose of from about 30 Gy to about 60 Gy. In further embodiments, the ionizing radiation can be administered at 2 Gy per dose for a total cumulative dose of from about 40 Gy to about 60 Gy. In still further embodiments, the ionizing radiation can be administered at 2 Gy per dose for a total cumulative dose of from about 45 Gy to about 55 Gy. In still further embodiments, the ionizing radiation can be administered at 2 Gy per dose for a total cumulative dose of from about 44 Gy to about 50 Gy. In optional embodiments, the ionizing radiation can be administered at 5 Gy per dose for a total cumulative dose of from about 15 Gy to about 30 Gy. In still further embodiments, the ionizing radiation can be administered at 5 Gy per dose for a total cumulative dose of from about 20 Gy to about 30 Gy. In another embodiment, the ionizing radiation can be administered at 5 Gy per dose for a total cumulative dose of about 25 Gy.

In other embodiments, the methods described above of treating a subject with colorectal cancer further comprises the step of administering to the subject in need thereof one or more doses of 5-fluorouracil (5-FU). In some embodiments the 5-FU is administered at an individual dose of from about 100 mg/m$^2$ to about 2,000 mg/m$^2$. In other embodiments the 5-FU is administered at an individual dose of from about 200 mg/m$^2$ to about 1,500 mg/m$^2$. In other embodiments the 5-FU is administered at an individual dose of from about 150 mg/m$^2$ to about 300 mg/m$^2$. In other embodiments the 5-FU is administered at an individual dose of from about 200 mg/m$^2$ to about 250 mg/m$^2$. In different individual embodiments, the 5-FU is administered in distinct doses selected independently from 100 mg/m$^2$, 200 mg/m$^2$, 225 mg/m$^2$, 250 mg/m$^2$, 300 mg/m$^2$, 400 mg/m$^2$, 500 mg/m$^2$, 600 mg/m$^2$, 700 mg/m$^2$, 800 mg/m$^2$, 900 mg/m$^2$, 1,000 mg/m$^2$, 1,100 mg/m$^2$, 1,200 mg/m$^2$, 1,300 mg/m$^2$, 1,400 mg/m$^2$, and 1,500 mg/m$^2$. Each of the individual doses and dose ranges listed for 5-FU may be administered as a bolus dose or as a protracted venous infusion (PVI), such as over a 12-hour or 24-hour period. As an example, an individual dose of 225 mg/m$^2$ can be administered to a subject in need thereof as a single bolus or over a 12-24 hour period via PVI. The dosing of 5-FU in the embodiments herein include further embodiments in which the 5-FU administration occurs during or contemporaneous with the administration of ionizing radiation therapy. Also included are embodiments in which the 5-FU administration to the subject in need thereof is administered at a time before and after administration of the ionizing radiation. For instance, the 5-FU administration can occur 7 days, 14 days, 21 days, or 28 days prior to and following administration of ionizing radiation.

5-FU may also be administered in combination with other agents, such as 5-FU plus leucovorin (WELLCOVERIN®), 5-FU with leucovorin and oxaliplatin (FOLFOX), and 5-FU with leucovorin and irinotecan (FOLFORI).

Other chemotherapeutic agents that may be used in combinations with the agents referenced herein include capecitabine (XELODA®), Irinotecan (CAMPTOSAR®), oxaliplatin (ELOXATIN®), and trifluridine with tipiracil (LONSURF®), capecitabine with irinotecan (XELIRI/CAPIRI), and capecitabine with oxaliplatin (XELOX/CAPEOX).

Chemotherapeutic agents in the methods herein can also be administered in combination with other targeted therapy drugs, such as vascular endothelial growth factor (VEGF) inhibitors, such as bevacizumab (AVASTIN®), ramucirumab (ACYRAMZA®), and ziv-aflibercept (ZALTRAP®), Epidermal growth factor receptor (EGFR) inhibitors, such as cetuximab (ERBITUX®) and panitumumab (VECTIBIX®), and kinase inhibitors, such as regorafenib (STIVARGA®).

Also provided is a method of predicting whether a colorectal tumor in a subject will be sensitive to or resistant to ionizing radiation, the method comprising:

receiving a sample comprising colorectal cancer cells from the colorectal tumor, where the colorectal cancer cells have been exposed to ionizing radiation;

measuring the RNA expression of a first biomarker comprising one or more of miR-451a, miR-1322, miR-133-3p, miR-1, miR-205-5p, miR-4521, CAB39, EMSY, or MEX3C in the sample; and measuring the RNA expression of the first biomarker in a non-irradiated control;

where RNA expression of miR-451a, miR-1322, miR-133-3p, or miR-1 in the sample that is greater than RNA expression of mir-451a, miR-1322, miR-133-3p, or miR-1 in the control is an indication that the colorectal tumor will be sensitive to ionizing radiation and where RNA expression of miR-205-5p, miR-4521, CAB39, EMSY, or MEX3C in the sample that is greater than the RNA expression of miR-205-5p, miR-4521, CAB39, EMSY, or MEX3C in the control is an indication that the colorectal tumor will be resistant to ionizing radiation.

In one embodiment, the measurement of RNA expression in the methods above is accomplished by reverse transcription polymerase chain reaction (RTPCR).

Definitions

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCR Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." In addition, the materials, methods, and examples are illustrative only and not intended to be limiting. In order to facilitate review of the various embodiments of the disclosure, the following explanations of specific terms are provided:

Administration: To provide or give a subject an agent, such as a composition comprising an effective amount of a pharmaceutical composition comprising miR-451a. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

Amplifying a polynucleotide: To increase the number of copies of a polynucleotide molecule, such as a gene or fragment of a gene, for example a region of a gene that encodes a tumor biomarker, such as miR-451a, miR-1322, miR-133-3p, miR-1, miR-205-5p, miR-4521, CAB39, EMSY, or MEX3C. The resulting products are called amplification products. An example of in vitro amplification is the polymerase chain reaction (PCR). Other examples of in vitro amplification techniques include quantitative real-time PCR, strand displacement amplification (see U.S. Pat. No. 5,744, 311); transcription-free isothermal amplification (see U.S. Pat. No. 6,033,881); repair chain reaction amplification (see WO90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025, 134).

A commonly used method for real-time quantitative polymerase chain reaction involves the use of a double stranded DNA dye (such as SYBR Green I dye). For example, as the amount of PCR product increases, more SYBR Green I dye binds to DNA, resulting in a steady increase in fluorescence. SYBR green binds to double stranded DNA, but not to single stranded DNA. In addition, SYBR green fluoresces strongly at a wavelength of 497 nm when it is bound to double stranded DNA, but does not fluoresce when it is not bound to double stranded DNA. As a result, the intensity of fluorescence at 497 nm may be correlated with the amount of amplification product present at any time during the reaction. The rate of amplification may in turn be correlated with the amount of template sequence present in the initial sample. Generally, Ct values are calculated similarly to those calculated using the TaqMan® system. Because the probe is absent, amplification of the proper sequence may be checked by any of a number of techniques. One such technique involves running the amplification products on an agarose or other gel appropriate for resolving polynucleotide fragments and comparing the amplification products from the quantitative real time PCR reaction with control DNA fragments of known size.

Another commonly used method is real-time quantitative TaqMan® PCR (Applied Biosystems). This type of PCR has reduced the variability traditionally associated with quantitative PCR, thus allowing the routine and reliable quantification of PCR products to produce sensitive, accurate, and reproducible measurements of levels of gene expression. The PCR step can use any of a number of thermostable DNA-dependent DNA polymerases, it typically employs a Taq DNA polymerase, which has a 5'-3' nuclease activity but lacks a 3'-5' proofreading endonuclease activity. Thus, TaqMan® PCR typically utilizes the 5'-nuclease activity of Taq or Tth polymerase to hydrolyze a hybridization probe bound to its target amplicon, but any enzyme with equivalent 5' nuclease activity can be used.

Two oligonucleotide primers are used to generate an amplicon typical of a PCR reaction. A third oligonucleotide, or probe, is designed to detect nucleotide sequence located between the two PCR primers. The probe is nonextendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

Examples of fluorescent labels that may be used in quantitative PCR include but need not be limited to: HEX, TET, 6-FAM, JOE, Cy3, Cy5, ROX TAMRA, and Texas Red. Examples of quenchers that may be used in quantitative PCR include, but need not be limited to TAMRA (which may be used as a quencher with HEX, TET, or 6-FAM), BHQ1, BHQ2, or DABCYL. TAQMAN® RT-PCR can be performed using commercially available equipment, such as, for example, ABI PRISM 7700® Sequence Detection System (Perkin-Elmer—Applied Biosystems), or Lightcycler (Roche Molecular Biochemicals).

In one embodiment, the 5' nuclease procedure is run on a real-time quantitative PCR device such as the ABI PRISM 7700® Sequence Detection System. The system includes a thermocycler, laser, charge-coupled device (CCD), camera and computer. The system amplifies samples in a 96-well format on a thermocycler. During amplification, laser-induced fluorescent signal is collected in real time through fiber optic cables for all 96 wells, and detected at the CCD. The system includes software for running the instrument and for analyzing the data. In some examples, 5'-nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct). To minimize errors and the effect of sample-to-sample variation, RT-PCR can be performed using an internal standard. The ideal internal standard is expressed at a constant level among different tissues, and is unaffected by the experimental treatment. RNAs most frequently used to normalize patterns of gene expression are the mRNA products of housekeeping genes such as GADPH, actin, and others.

Amplification of a polynucleotide sequence may be used for any of a number of purposes, including increasing the amount of a rare sequence to be analyzed by other methods. It may also be used to identify a sequence directly (for example, though an amplification refractory mutation system) or as part of a DNA sequencing method.

Array: An arrangement of molecules, such as biological macromolecules (such as peptides or polynucleotide molecules) or biological samples (such as tissue sections), in addressable locations on or in a substrate. A "microarray" is an array that is miniaturized so as to require or be aided by microscopic examination for evaluation or analysis. In certain example arrays, one or more molecules (such as an antibody or peptide) will occur on the array a plurality of times (such as twice), for instance to provide internal controls. The number of addressable locations on the array can vary, for example from at least one, to at least 2, to at least 3, at least 4, at least 5, at least 6, at least 10, at least 20, at least 30, at least 50, at least 75, at least 100, at least 150, at least 200, at least 300, at least 500, least 550, at least 600, at least 800, at least 1000, at least 10,000, or more. In some examples, arrays include positive and/or negative controls, such as probes that bind housekeeping genes. In particular examples, an array includes polynucleotide molecules, such as oligonucleotide sequences that are at least 15 nucleotides in length, such as about 15-75 or 15-60 nucleotides in length. In particular examples, an array includes oligonucleotide probes or primers which can be used to detect nucleotides that encode tumor biomarker sequences (including RCC biomarkers). In an example, the array is a commercially available array such as Human Genome GeneChip® arrays from Affymetrix (Santa Clara, Calif.).

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays may be computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Biomarker: Molecular, biological or physical attributes that characterize a physiological or cellular state and that can be objectively measured to detect or define disease progression or predict or quantify therapeutic responses. A biomarker is a characteristic that is objectively measured and evaluated as an indicator of normal biologic processes, pathogenic processes, or pharmacologic responses to a therapeutic intervention. A biomarker may be any molecular structure produced by a cell or organism. A biomarker may be expressed inside any cell or tissue; accessible on the surface of a tissue or cell; structurally inherent to a cell or tissue such as a structural component, secreted by a cell or tissue, produced by the breakdown of a cell or tissue through processes such as necrosis, apoptosis or the like; or any combination of these. A biomarker may be any protein, carbohydrate, fat, nucleic acid, catalytic site, or any combination of these such as an enzyme, glycoprotein, cell membrane, virus, cell, organ, organelle, or any uni- or multimolecular structure or any other such structure now known or yet to be disclosed whether alone or in combination.

A biomarker can be represented by the sequence of a polynucleotide from which it can be derived, a polypeptide, or any other chemical structure. Examples of polynucleotides include miRNA, tRNA, siRNA, mRNA, cDNA, or genomic DNA sequences including any complimentary sequences thereof. One example of a biomarker is a DNA coding sequence for a protein comprising one or more mutations that cause amino acid substitutions in the protein sequence.

Cancer: A disease or condition in which abnormal cells divide without control and are able to invade other tissues. Cancer cells spread to other body parts through the blood and lymphatic systems. Cancer is a term for many diseases. There are more than 100 different types of cancer in humans. Most cancers are named after the organ in which they originate. For instance, a cancer that begins in the colon may be called a colon cancer. However, the characteristics of a cancer, especially with regard to the sensitivity of the cancer to therapeutic compounds, are not limited to the organ in which the cancer originates. A cancer cell is any cell derived from any cancer, whether in vitro or in vivo.

Cancer cells form tumors characterized by abnormal or uncontrolled cell growth. Other features often associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc.

"Metastatic disease" or "metastasis" refers to cancer cells that have left the original tumor site and migrate to other parts of the body for example via the bloodstream or lymph system. The "pathology" of cancer includes all phenomena that compromise the wellbeing of the subject. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

Cancers include hematological malignancies which are cancers of the hematopoietic system including leukemias, lymphomas, and other such malignancies. Colorectal cancers include colorectal adenocarcinomas, along with mucinous adenocarcinomas, Signet ring cell carcinomas, gastrointestinal carcinoid tumors, gastrointestinal stromal tumors leiomyosarcomas, melanomas, and primary colorectal lymphomas Control: A reference standard. As disclosed herein, a control can be a negative control such as a microRNA mimic. Such a mimic can be an oligoribonucleotide not known to silence any known gene and particularly genes silenced by miR-451a.

Effective amount: As used herein, the terms "effective amount", "therapeutically effective amount", or "pharmaceutically effective amount", refer to an amount of an agent, such as a pharmaceutical composition comprising miR-451a that is sufficient to generate a desired response, such as reduce or eliminate a sign or symptom of a condition or disease such as insensitivity to ionizing radiation. In some examples, an "effective amount" is one that treats (including prophylaxis) one or more symptoms and/or underlying causes of any of a disorder or disease. An effective amount can be a therapeutically effective amount, including an amount that prevents one or more signs or symptoms of a particular disease or condition from developing, such as one or more signs or symptoms associated with cancer, particularly cancer characterized by resistance to ionizing radiation. In some embodiments herein a pharmaceutically effective amount of miR-451a includes individual doses in humans of from about 0.1 mg/kg to about 20 mg/kg. In other embodiments, a pharmaceutically effective amount of miR-451a includes individual doses in humans of from about 0.1 mg/kg to about 15 mg/kg. In further embodiments, a pharmaceutically effective amount of miR-451a includes individual doses in humans of from about 0.1 mg/kg to about 12 mg/kg. In other embodiments, a pharmaceutically effective amount of miR-451a includes individual doses in humans of from about 0.1 mg/kg to about 10 mg/kg. In still other embodiments, a pharmaceutically effective amount of miR-451a includes individual doses in humans of from about 0.1 mg/kg to about 7.5 mg/kg. In additional embodiments, a pharmaceutically effective amount of miR-451a includes individual doses in humans of from about 0.1 mg/kg to about 5 mg/kg. In separate embodiments, miR-451a may be administered in individual doses selected from the group of 0.5 mg/kg, 1 mg/kg, 2 mg/kg, 3 mg/kg, 4 mg/kg, 5 mg/kg, 6 mg/kg, 7 mg/kg, 8 mg/kg, 9 mg/kg, and 10 mg/kg.

In some embodiments, the administration of miR-451a to the subject in need thereof would occur prior to administration of ionizing radiation. In one embodiment the effective amount of miR-451a is administered to the subject in need thereof from about one day to about thirty days prior to the administration of ionizing radiation. In another embodiment, the effective amount of miR-451a is administered to the subject in need thereof from about two days to about thirty days prior to the administration of ionizing radiation. In separate embodiments, the effective amount of miR-451a is administered to the subject in need thereof about five days, about 7 days, about 10 days, about 14 days, about 15 days, about 20 days, about 21 days, about 25 days, about 28 days or about 30 days prior to the administration of ionizing radiation.

Expression: The process by which the coded information of a gene is converted into an operational, non-operational, or structural part of a cell, such as the synthesis of RNA such as a microRNA or messenger RNA from the gene.

MicroRNA: MicroRNAs are a major class of biomolecules involved in control of gene expression. For example, in human heart, liver or brain, miRNAs play a role in tissue specification or cell lineage decisions. In addition, miRNAs influence a variety of processes, including early development, cell proliferation and cell death, and apoptosis and fat metabolism. The large number of miRNA genes, the diverse expression patterns and the abundance of potential miRNA targets suggest that miRNAs may be a significant source of genetic diversity.

A mature miRNA is typically an 18-25 nucleotide non-coding RNA that regulates expression of an mRNA including sequences complementary to the miRNA. These small RNA molecules are known to control gene expression by regulating the stability and/or translation of mRNAs. For example, miRNAs bind to the 3' UTR of target mRNAs and suppress translation. MiRNAs may also bind to target mRNAs and mediate gene silencing through the RNAi pathway. MiRNAs may also regulate gene expression by causing chromatin condensation.

A miRNA silences translation of one or more specific mRNA molecules by binding to a miRNA recognition element (MRE,) which is defined as any sequence that directly base pairs with and interacts with the miRNA somewhere on the mRNA transcript. Often, the MRE is present in the 3' untranslated region (UTR) of the mRNA, but it may also be present in the coding sequence or in the 5' UTR. MREs are not necessarily perfect complements to miRNAs, usually having only a few bases of complementarity to the miRNA and often containing one or more mismatches within those bases of complementarity. The MRE may be any sequence capable of being bound by a miRNA sufficiently that the translation of a gene to which the MRE is operably linked is repressed by a miRNA silencing mechanism such as the RISC. A microRNA can interchangeably be abbreviated to 'miRNA' or 'miR'.

Operably Linked: A first nucleic acid sequence is operably linked with a second nucleic acid sequence when the first nucleic acid sequence is placed in such a way that it has an effect upon the second nucleic acid sequence. For instance, a MRE is operably linked to a coding sequence that it silences if binding of the miRNA to the MRE silences the expression of the coding sequence. Operably linked DNA sequences may be contiguous, or they may operate at a distance. Additionally a promoter sequence is operably linked to a DNA coding sequence if the promoter, when bound to an appropriate polymerase, drives mRNA expression of the coding sequence.

Pharmaceutically acceptable carriers: The pharmaceutically acceptable carriers of use are conventional. Remington's Pharmaceutical Sciences, by E. W. Martin, Mack Publishing Co., Easton, Pa., 19th Edition, 1995, describes compositions and formulations suitable for pharmaceutical delivery of the compositions disclosed herein. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: a nucleic acid polymer. A deoxyribonucleotide or ribonucleotide polymer including, without limitation, cDNA, mRNA, genomic DNA, methylated DNA, and synthetic (such as chemically synthesized) nucleic acids such as DNA, RNA, and/or methylated oligonucleotides. The polynucleotide molecule can be double-stranded or single-stranded. Where single-stranded, the nucleic acid molecule can be the sense strand or the anti-sense strand. In addition, nucleic acid molecule can be circular or linear. A polynucleotide molecule may also be termed a nucleic acid and the terms are used interchangeably.

Promoter: A promoter may be any of a number of nucleic acid control sequences that directs transcription of a nucleic acid. Typically, a eukaryotic promoter includes necessary nucleic acid sequences near the start site of transcription, such as, in the case of a polymerase II type promoter, a TATA element or any other specific DNA sequence that is recognized by one or more transcription factors. Expression by a promoter may be further modulated by enhancer or repressor elements. Numerous examples of promoters are available and well known to those of skill in the art. A nucleic acid comprising a promoter operably linked to a nucleic acid sequence that codes for a particular polypeptide can be termed an expression vector.

Recombinant: A recombinant nucleic acid or polypeptide is one that has a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques. A recombinant polypeptide can also refer to a polypeptide that has been made using recombinant nucleic acids, including recombinant nucleic acids transferred to a host organism that is not the natural source of the polypeptide.

Sample (or biological sample): A biological specimen containing cells, particularly cancer cells, and particularly cancer cells that contain nucleic acid that is obtained from a subject.

Subject: A living multicellular vertebrate organism, a category that includes, for example, mammals and birds. A "mammal" includes both human and non-human mammals, such as mice and non-human primates. In some examples, a subject is a human patient, such as a patient diagnosed with cancer. In other examples, a subject is a human patient yet to be diagnosed with cancer.

Treatment: As used herein, the term "treatment" refers to an intervention that ameliorates a sign or symptom of a disease or pathological condition. As used herein, the terms "treatment", "treat" and "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed.

Disclosed herein is a pharmaceutical composition comprising an effective amount of one or more microRNAs of miR-451a, miR-1322 and a pharmaceutically acceptable carrier. Also disclosed are methods of treating a cancer characterized by aberrant MRN complex activity comprising administering such a pharmaceutical composition.

miRNA

A microRNA silences translation of one or more specific mRNA molecules by binding to a microRNA recognition element (MRE,) which is defined as any sequence that directly base pairs with and interacts with the microRNA somewhere on the mRNA transcript. Often, the MRE is present in the 3' untranslated region (UTR) of the mRNA, but it may also be present in the coding sequence or in the 5' UTR. MREs are not necessarily perfect complements to microRNAs, usually having only a few bases of complementarity to the microRNA and often containing one or more mismatches within those bases of complementarity. As a result, microRNA-mRNA interactions are difficult to predict. The MRE may be any sequence capable of being bound by a microRNA sufficiently that the translation of the target mRNA is repressed by a microRNA silencing mechanism such as the RISC.

miRNA molecules can be provided in several forms including, e.g., as one or more isolated miRNA duplexes, as longer double-stranded RNA (dsRNA), or as miRNA or dsRNA transcribed from a transcriptional cassette in a DNA plasmid. The miRNA sequences may have overhangs (as 3' or 5' overhangs as described in Elbashir et al, *Genes Dev* 15, 188 (2001) or Nykänen et al, *Cell* 107, 309 (2001)) or may lack overhangs (i.e., have blunt ends).

One or more DNA plasmids encoding one or more miRNA templates may be used to provide miRNA. miRNA can be transcribed as sequences that automatically fold into duplexes with hairpin loops from DNA templates in plasmids having RNA polymerase III transcriptional units, for example, based on the naturally occurring transcription units for small nuclear RNA U6 or human RNase P RNA H1 (Brummelkamp et al, *Science* 296, 550 (2002); Donzé et al, *Nucleic Acids Res* 30, e46 (2002); Paddison et al, *Genes Dev* 16, 948 (2002); Yu et al, *Proc Natl Acad Sci USA* 99, 6047 (2002); Lee et al, *Nat Biotech*, 20, 500 (2002); Miyagishi et al, *Nat Biotech* 20, 497 (2002); Paul et al, *Nat Biotech,* 20, 505 (2002); and Sui et al, *Proc Natl Acad Sci USA,* 99, 5515 (2002)). Typically, a transcriptional unit or cassette will contain an RNA transcript promoter sequence, such as an H1-RNA or a U6 promoter, operably linked to a template for transcription of a desired miRNA sequence and a termination sequence, comprised of 2-3 uridine residues and a polythymidine (T5) sequence (polyadenylation signal) (Brummelkamp et al (2002) supra). The selected promoter can provide for constitutive or inducible transcription. Compositions and methods for DNA-directed transcription of RNA interference molecules are described in detail in U.S. Pat. No. 6,573,099. The transcriptional unit is incorporated into a plasmid or DNA vector from which the interfering RNA is transcribed. Plasmids suitable for in vivo delivery of genetic material for therapeutic purposes are described in detail in U.S. Pat. Nos. 5,962,428 and 5,910,488. The selected plasmid can provide for transient or stable delivery of a nucleic acid to a target cell. It will be apparent to those of skill in the art that plasmids originally designed to express desired gene sequences can be modified to contain a transcriptional unit cassette for transcription of miRNA.

Methods for isolating RNA, synthesizing RNA, hybridizing nucleic acids, making and screening cDNA libraries, and performing PCR are well known in the art (see, e.g., Gubler and Hoffman, *Gene* 25, 263-269 (1983); Sambrook and Russell, *Molecular Cloning: A Laboratory Manual*, Cold Spring Harbor Laboratory Press, Cold Spring Harbor N.Y., (2001)) as are PCR methods (see, U.S. Pat. Nos. 4,683,195 and 4,683,202; *PCR Protocols: A Guide to Methods and Applications*, Innis et al, eds, (1990)). Expression libraries are also well known to those of skill in the art. Additional basic texts disclosing the general methods of use in this invention include Sambrook and Russell (2001) supra; Kriegler, *Gene Transfer and Expression: A Laboratory Manual* (1990); and *Current Protocols in Molecular Biology* (Ausubel et al., eds., 1994).

A miRNA molecule can be chemically synthesized. A single-stranded nucleic acid that includes an miRNA sequence can be synthesized using any of a variety of techniques known in the art, such as those described in Usman et al, *J Am Chem Soc,* 109, 7845 (1987); Scaringe et al, *Nucl Acids Res,* 18, 5433 (1990); Wincott et al, *Nucl Acids Res,* 23, 2677-2684 (1995); and Wincott et al, *Methods Mol Bio* 74, 59 (1997). Synthesis of the single-stranded nucleic acid makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 micromolar scale protocol with a 2.5 min coupling step for 2'-O-methylated nucleotides. Alternatively, syntheses at the 0.2 micromolar scale can be performed on a 96-well plate synthesizer from Protogene. However, a larger or smaller scale of synthesis is encompassed by the invention, including any method of synthesis now known or yet to be disclosed. Suitable reagents for synthesis of the miRNA single stranded molecules, methods for RNA deprotection, and methods for RNA purification are known to those of skill in the art.

A double stranded miRNA can also be synthesized via a tandem synthesis technique, wherein both strands are synthesized as a single continuous fragment or strand separated by a linker that is subsequently cleaved to provide separate fragments or strands that hybridize to form a duplex. The linker may be any linker, including a polynucleotide linker or a non-nucleotide linker. The tandem synthesis of miRNA can be readily adapted to both multiwell/multiplate synthesis platforms as well as large scale synthesis platform employing batch reactors, synthesis columns, and the like. Alternatively, the miRNA can be assembled from two distinct single-stranded molecules, wherein one strand includes the sense strand and the other includes the antisense strand of the miRNA. For example, each strand can be synthesized separately and joined together by hybridization or ligation following synthesis and/or deprotection. Either the sense or the antisense strand can contain additional nucleotides that are not complementary to one another and do not form a double stranded miRNA. In certain other instances, the miRNA molecules can be synthesized as a single continuous fragment, where the self-complementary sense and antisense regions hybridize to form a miRNA duplex having hairpin secondary structure.

An miRNA molecule may comprise a duplex having two complementary strands that form a double-stranded region with least one modified nucleotide in the double-stranded region. The modified nucleotide may be on one strand or both. If the modified nucleotide is present on both strands, it may be in the same or different positions on each strand. A modified miRNA may be less immunostimulatory than a corresponding unmodified miRNA sequence, but retains the capability of silencing the expression of a target sequence.

Examples of modified nucleotides suitable for use in the present invention include, but are not limited to, ribonucleotides having a 2'-O-methyl (2'OMe), 2'-deoxy-2'-fluoro (2'F), 2'-deoxy, 5-C-methyl, 2'-O-(2-methoxyethyl) (MOE), 4'-thio, 2'-amino, or 2'-C-allyl group. Modified nucleotides having a conformation such as those described in the art, for example in Saenger, *Principles of Nucleic Acid Structure*, Springer-Verlag Ed. (1984), are also suitable for use in miRNA molecules. Other modified nucleotides include, without limitation: locked nucleic acid (LNA) nucleotides, G-clamp nucleotides, or nucleotide base analogs. LNA nucleotides include but need not be limited to 2'-O, 4'-Cm-ethylene-(D-ribofuranosyl)nucleotides), 2'-O-(2-methoxy-ethyl) (MOE) nucleotides, 2'-methyl-thio-ethyl nucleotides, 2'-deoxy-2'-fluoro (2'F) nucleotides, 2'-deoxy-2'-chloro (2Cl) nucleotides, and 2'-azido nucleotides. A G-clamp nucleotide refers to a modified cytosine analog wherein the modifications confer the ability to hydrogen bond both Watson-Crick and Hoogsteen faces of a complementary guanine nucleotide within a duplex (Lin et al, *J Am Chem Soc,* 120, 8531-8532 (1998)). Nucleotide base analogs include for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (Loakes, *Nucl Acids Res,* 29, 2437-2447 (2001)).

A miRNA molecule may comprise one or more chemical modifications such as terminal cap moieties, phosphate backbone modifications, and the like. Examples of classes of terminal cap moieties include, without limitation, inverted deoxy abasic residues, glyceryl modifications, 4',5'-methylene nucleotides, 1-(β-D-erythrofuranosyl) nucleotides, 4'-thio nucleotides, carbocyclic nucleotides, 1,5-anhydrohexitol nucleotides, L-nucleotides, α-nucleotides, modified base nucleotides, threopentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-aminoalkyl phosphate, 1,3-diamino-2-propyl phosphate, 3-aminopropyl phosphate, 6-aminohexyl phosphate, 1,2-aminododecyl phosphate, hydroxypropyl phosphate, 1,4-butanediol phosphate, 3'-phosphoramidate, 5'phosphoramidate, hexylphosphate, aminohexyl phosphate, 3'-phosphate, 5'-amino, 3'-phosphorothioate, 5'-phosphorothioate, phosphorodithioate, and bridging or nonbridging methylphosphonate or 5'-mercapto moieties (see, e.g., U.S. Pat. No. 5,998,203; Beaucage et al, *Tetrahedron* 49, 1925 (1993)). Non-limiting examples of phosphate backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al, *Modern Synthetic Methods*, VCH, 331-417 (1995); Mesmaeker et al, *Antisense Research*, ACS, 24-39 (1994)). Such chemical modifications can occur at the 5'-end and/or 3'-end of the sense strand, antisense strand, or both strands of the miRNA.

The sense and/or antisense strand of a miRNA may comprise a 3'-terminal overhang having 1 to 4 or more 2'-deoxyribonucleotides and/or any combination of modified and unmodified nucleotides. Additional examples of modified nucleotides and types of chemical modifications that can be introduced into the modified miRNA molecules of the present invention are described, e.g., in UK Patent No. GB 2,397,818 B and U.S. Patent Publication Nos. 20040192626 and 20050282188.

A miRNA molecule may comprise one or more non-nucleotides in one or both strands of the miRNA. A non-nucleotide may be any subunit, functional group, or other molecular entity capable of being incorporated into a nucleic acid chain in the place of one or more nucleotide units that is not or does not comprise a commonly recognized nucleotide base such as adenosine, guanine, cytosine, uracil, or thymine, such as a sugar or phosphate.

Chemical modification of the miRNA may also comprise attaching a conjugate to the miRNA molecule. The conjugate can be attached at the 5'- and/or the 3'-end of the sense and/or the antisense strand of the miRNA via a covalent attachment such as a nucleic acid or non-nucleic acid linker. The conjugate can also be attached to the miRNA through a carbamate group or other linking group (see, e.g., U.S. Patent Publication Nos. 20050074771, 20050043219, and 20050158727). A conjugate may be added to the miRNA for any of a number of purposes. For example, the conjugate may be a molecular entity that facilitates the delivery of the miRNA into a cell or the conjugate a molecule that comprises a drug or label. Examples of conjugate molecules suitable for attachment to the miRNA of the present invention include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples of conjugate molecules include a hydrophobic group, a membrane active compound, a cell penetrating compound, a cell targeting signal, an interaction modifier, or a steric stabilizer as described in U.S. Patent Publication No. 20040167090. Further examples include the conjugate molecules described in U.S. Patent Publication No. 20050239739.

The type of conjugate used and the extent of conjugation to the miRNA can be evaluated for improved pharmacokinetic profiles, bioavailability, and/or stability of the miRNA while retaining activity. As such, one skilled in the art can screen miRNA molecules having various conjugates attached thereto to identify miRNA conjugates having improved properties using any of a variety of well-known in vitro cell culture or in vivo animal models.

A miRNA may be incorporated into a carrier systems containing the miRNA molecules described herein. The carrier system can be a lipid-based carrier system such as a stabilized nucleic acid-lipid particle 5 (e.g., SNALP or SPLP), cationic lipid or liposome nucleic acid complexes (i.e., lipoplexes), a liposome, a micelle, a virosome, or a mixture thereof. In other embodiments, the carrier system is a polymer-based carrier system such as a cationic polymer-nucleic acid complex (i.e., polyplex). In additional embodiments, the carrier system is a cyclodextrin-based carrier system such as a cyclodextrin polymer-nucleic acid complex (see US Patent Application Publication 20070218122). In further embodiments, the carrier system is a protein-based carrier system such as a cationic peptide-nucleic acid complex. A miRNA molecule can also be delivered as modified or unmodified naked miRNA.

Pharmaceutical Compositions

The miRNA compounds disclosed herein may be included in pharmaceutical compositions (including therapeutic and prophylactic formulations), typically combined together with one or more pharmaceutically acceptable carriers (known equivalently as vehicles) and, optionally, other therapeutic ingredients.

Such pharmaceutical compositions can formulated for administration to subjects by a variety of mucosal administration modes, including by oral, rectal, intranasal, intrapulmonary, intravitrial, or transdermal delivery, or by topical delivery to other surfaces including the eye. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other examples, the compound can be administered ex vivo by direct exposure to cells, tissues or organs originating from a subject.

To formulate the pharmaceutical compositions, the compound can be combined with various pharmaceutically acceptable additives. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween®-80), solubility enhancing agents (for example, cyclodextrins and derivatives thereof), stabilizers (for example, serum albumin), and reducing agents (for example, glutathione) can be included.

When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7. The compound can be dispersed in any pharmaceutically acceptable carrier, which can include a hydrophilic compound having a capacity to disperse the compound, and any desired additives. The carrier can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a carrier, for example, polylactic acid, poly(lactic acid-glycolic acid) copolymer, polyhydroxybutyric acid, poly(hydroxybutyric acid glycolic acid) copolymer and mixtures thereof.

Alternatively or additionally, synthetic fatty acid esters such as polyglycerin fatty acid esters, sucrose fatty acid esters and the like can be employed as carriers. Hydrophilic polymers and other vehicles can be used alone or in combination, and enhanced structural integrity can be imparted to the vehicle by partial crystallization, ionic bonding, cross-linking and the like. The carrier can be provided in a variety of forms, including fluid or viscous solutions, gels, pastes, powders, microspheres, and films for direct application to a mucosal surface.

The compound can be combined with the carrier according to a variety of methods, and release of the compound can be by diffusion, disintegration of the vehicle, or associated formation of water channels. In some circumstances, the compound is dispersed in microcapsules (microspheres) or nanoparticles prepared from a suitable polymer, for example, 5-isobutyl 2-cyanoacrylate (see, for example, Michael et al., *J. Pharmacy Pharmacol.* 43, 1-5, (1991), and dispersed in a biocompatible dispersing medium, which yields sustained delivery and biological activity over a protracted time.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acidco-glycolic acid), poly(D-lactic acid-co-glycolic acid), and poly(L-lactic acid-coglycolic acid). Other useful biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (betahydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, Sustained and Controlled Release Drug Delivery Systems, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675, 189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

miR in Colorectal Cancer

Several recent studies have shown the utility of miRs in the diagnosis and classification of CRC (Kanaan Z et al, Ann Surg 258, 400 (2013); Tsikitis V L et al, Cancer Prev Res 2016; Tsikitis V L et al, Am J Surg 207, 717 (2014); and Vychytilova-Faltejskova P et al, Carcinogenesis 37, 941 (2016); all of which are incorporated by reference herein). There are ongoing prospective clinical trials evaluating miR based classifiers such as a 24-miR signature in lung cancer diagnosis (Sestini S et al, Oncotarget 6, 32868 (2015); incorporated by reference herein) (Gensignia) and a miR signature in prostate cancer screening Kristensen H et al, Oncotarget 2016 (incorporated by reference herein) (Exiqon). These trials highlight the feasibility and translational potential of miR based classifiers. Disclosed herein is a group of miRs that are responsive to radiation in mouse xenograft models. miR-451a was characterized particularly as one of the robust early response miRs in CRC. The data disclosed in the examples below indicate that miR-451 behaves as a tumor suppressor in CRC cell lines in vitro. Putative targets of miR-451 were identified and expression of two of the targets was shown to correlate with overall survival in human colorectal cancer. Taken together, these observations suggest that miR-451a modulation of CAB39 and EMSY target genes could alter radiation sensitivity of human CRC.

miR-451a has been found to inhibit cell proliferation and drug responses in other malignancies. For example, miR-451a was found to affect proliferation and sensitivity to tamoxifen in breast cancer via targeting of the macrophage migration inhibitory factor (MIF) (Liu Z et al, Biomed Res Int 2015, 207685 (2015); incorporated by reference herein). Similarly, miR-451a was shown to be tumor suppressive in gastric cancer by affecting the PI3K/mTOR pathway Riquelme I et al, Cell Oncol 39, 23 (2016); incorporated by reference herein). In other tumor types, it has been shown that miR-451a expression is downregulated in the tumor cells in a manner consistent with a tumor suppressor function (Li M et al, PLoS One 10, e0135549 (2015) and Minna E et al, Oncotarget 7, 12731 (2016); both of which are incorporated by reference herein). Interestingly, miR-451a appears to increase radiation responses in nasopharyngeal carcinoma cells (Zhang T et al, Tumor Biol 35, 12593 (2014); incorporated by reference herein) and lung adenocarcinoma cells Tian F et al, Thoracic Cancer 7, 226 (2016); both of which are incorporated by reference herein. The observation that miR-451a is a tumor suppressor in CRC cell lines suggests a function similar to the tumor suppressive role that have been documented in other cancers by these studies.

Using a bioinformatics approach, the targets of miR-451a were narrowed to a group of 14 genes which in turn was narrowed to 4 genes—CAB39, EMSY, EREG and MEX3C based on either a known role in colorectal cancer or radiation responsiveness in other cancer types. Calcium binding protein (CAB) 39 has been previously shown to be a target of miR-451a in human glioma Tian Y et al, Int J Oncol 40, 1105 (2012); incorporated by reference herein). This protein is thought to affect STK11 activity and localization thereby influencing the PI3K/AKT signaling pathway. EMSY is a transcriptional repressor that associates with BRCA2 and is often amplified in breast and ovarian cancers (Hughes-Davies L et al, Cell 115, 523 (2003); incorporated by reference herein. Functionally, EMSY colocalizes and forms foci with histone γH2AX in response irradiation. Importantly, breast cancer patients with EMSY amplifications have poorer overall survival. Taken together, these functions suggest that modulation of EMSY by miR-451a may have significant impact on radiation responses and tumor cell survival. Indeed, consistent with the breast cancer dataset, the analysis of the TCGA colorectal cancer dataset (FIG. 5c-d) indicates that EMSY as well as CAB39 are increased at the protein level in a subset of patients and associated with worse outcome. Epiregulin (EREG) is a known ligand of the EGF family and regulates several key processes including cellular proliferation, inflammation, angiogenesis and wound healing Riese D J et al, Sem Cell Dev Biol 28, 49 (2014); incorporated by reference herein. While it has been proposed as a biomarker for monitoring responses to cetuximab in colorectal cancer (Jonker D J et al, Br J Cancer 110, 648 (2014); incorporated by reference herein), it is unclear whether there is a function for EREG specifically in the context of radiation responses of these tumors. MEX3C has been identified as a ubiquitin ligase as well as an RNA binding protein that modulates the levels of HLA-A allotypes (Cano F et al, EMBO J 31, 3596 (2012); incorporated by reference herein). Interestingly, it is part of a group of genes that suppress chromosomal instability in colorectal cancer (Burrell R A et al, Nature 494, 492 (2013); incorporated by reference herein) thereby likely contributing to tumor drug resistance.

The data disclosed herein indicates that miR-451a mRNA binds to all four of these mRNAs (FIG. 5a) and downregulates their expression at the RNA level. Due to low expression levels of the EREG and MEX3C in patient samples, CAB39 and EMSY expression was analyzed. The analysis showed a statistically significant reciprocal relationship between the miR-451 and these two target genes in the patient samples analyzed.

miR-451 is a radiation-induced miR in CRC its targets likely contribute to radiation responses. The disclosed data can result in of miR and/or target biomarkers that predict radiation responsiveness and can provide strategies for enhancing the effectiveness of chemoradiation in colorectal cancers.

EXAMPLES

The following examples are for illustration only. In light of this disclosure, those of skill in the art will recognize that variations of these examples and other examples of the disclosed invention be possible without undue experimentation.

Example 1—Early and Late Radiation Responsive miRs in CRC

To identify miRs that are regulated by radiation in CRC, either HCT-116 or SW-480 xenografts were implanted into nude mice. After the tumors grew to a 300 mm$^3$ volume, the mice were treated with a single 2 Gy dose of focal radiation. Tumors were harvested at either 6 h or 48 h post-radiation treatment and RNA was extracted to generate the initial in vivo miR profile using Affymetrix microRNA arrays. miRs that were either upregulated or downregulated by a factor of two in the presence of radiation were selected. This analysis identified two miRs that were upregulated and two miRs that were downregulated at 6 h (FIG. 1a). Of these, miR-451a was validated using qRT-PCR across three different human CRC cell lines (FIG. 1b) grown as subcutaneous xenografts.

Example 2—miR-451a Functions as a Tumor Suppressor miR in Colorectal Cancer

Figure 2A:
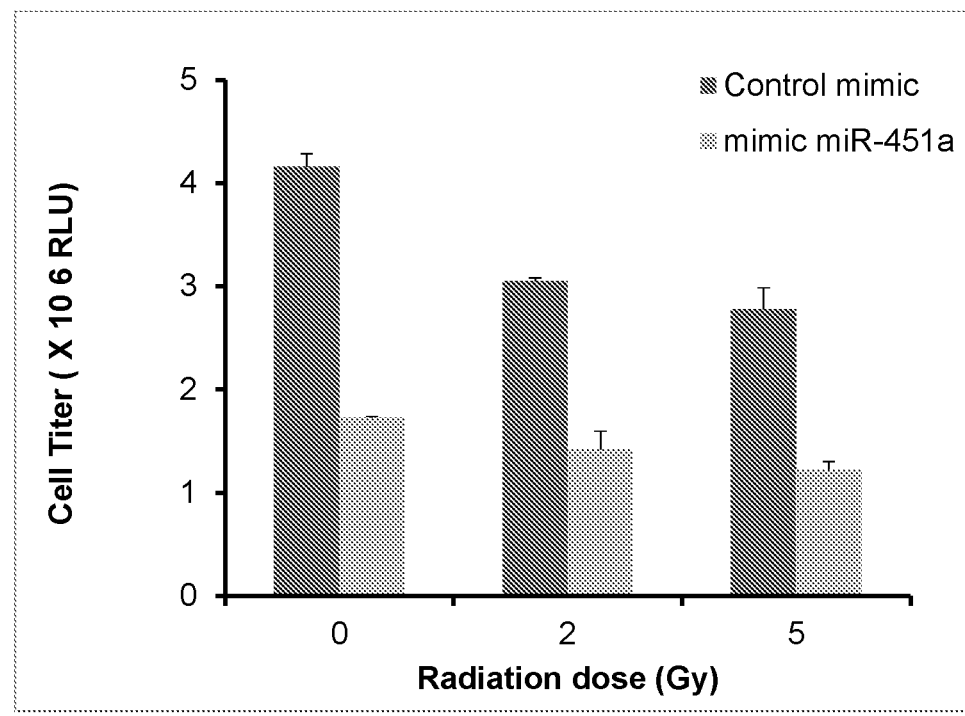
FIG. 2A is a graph showing results where HCT116 were transfected with a miR-451a mimic or a control mimic. Proliferation was analyzed 48 hours after radiation in 2D cultures with the indicated doses. Bars depict mean±s.e.m. of triplicate wells. ** indicates P<0.01 on a two-tailed Student's T-test.
Figure 2B:
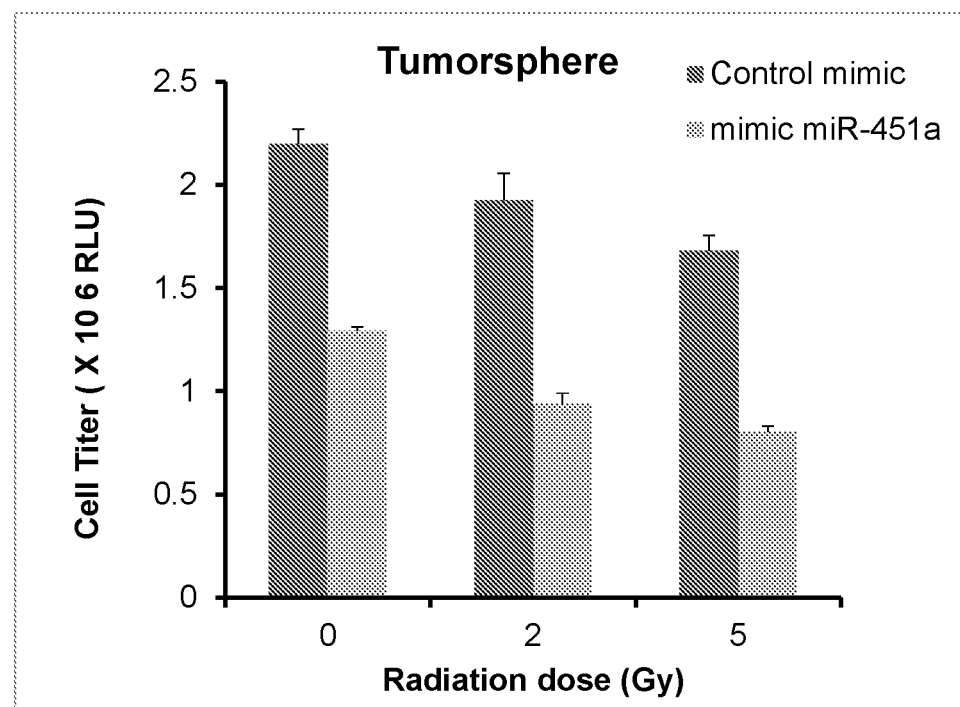
FIG. 2B is a graph showing results where HCT116 were transfected with a miR-451a mimic or a control mimic. Proliferation was analyzed 48 hours after radiation in 3D cultures with the indicated doses. Bars depict mean±s.e.m. of triplicate wells. ** indicates P<0.01 on a two-tailed Student's T-test.
Figure 2C:
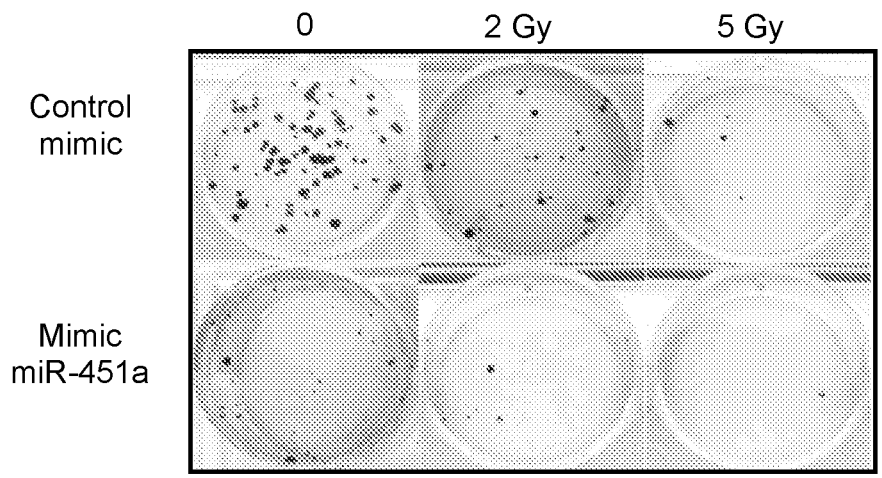
FIG. 2C is an image of the results where 12-14 days after plating, cells were fixed and stained with crystal violet and colonies were counted.
Figure 2D:
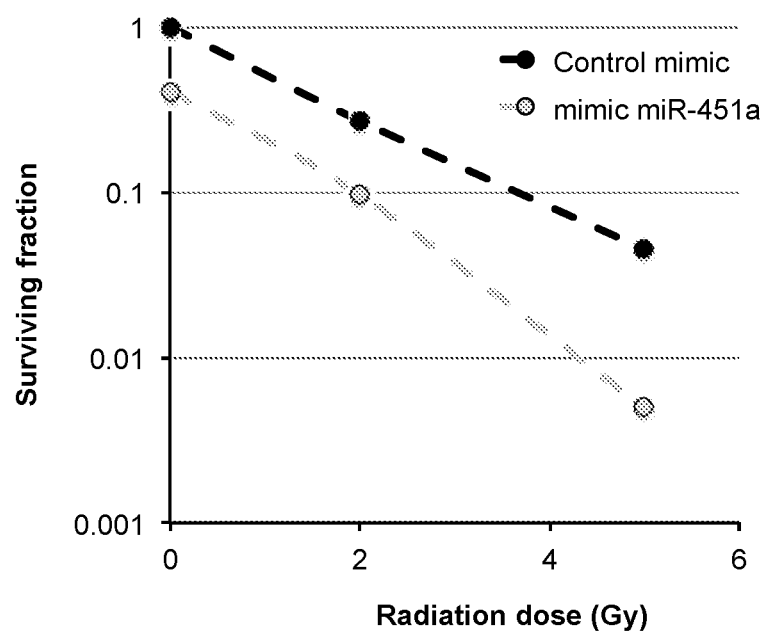
FIG. 2D is a plot of the results shown in FIG. 2C. The surviving fraction was calculated based on the colony numbers normalized to the plating efficiency. The mean of triplicate wells is plotted. * indicates P<0.05 and ** indicates P<0.01 on a two-tailed Student's T-test.
Figure 3A:
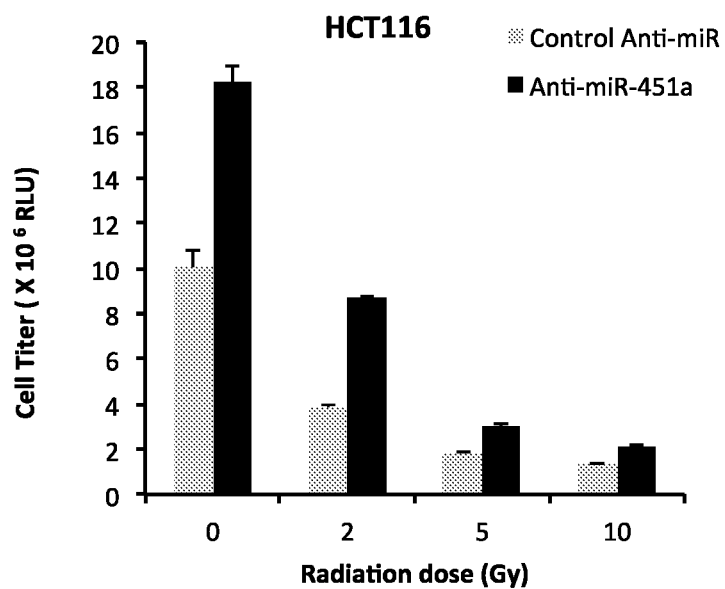
FIG. 3A is a graph showing results where HCT116 were transfected with a miR-451a inhibitor (anti-miR-451a) or a control anti-miR. Proliferation was analyzed 48 hours after radiation in 2D culture with the indicated doses. Bars depict mean±s.e.m. of triplicate wells. ** indicates P<0.01 on a two-tailed Student's T-test.
Figure 3B:
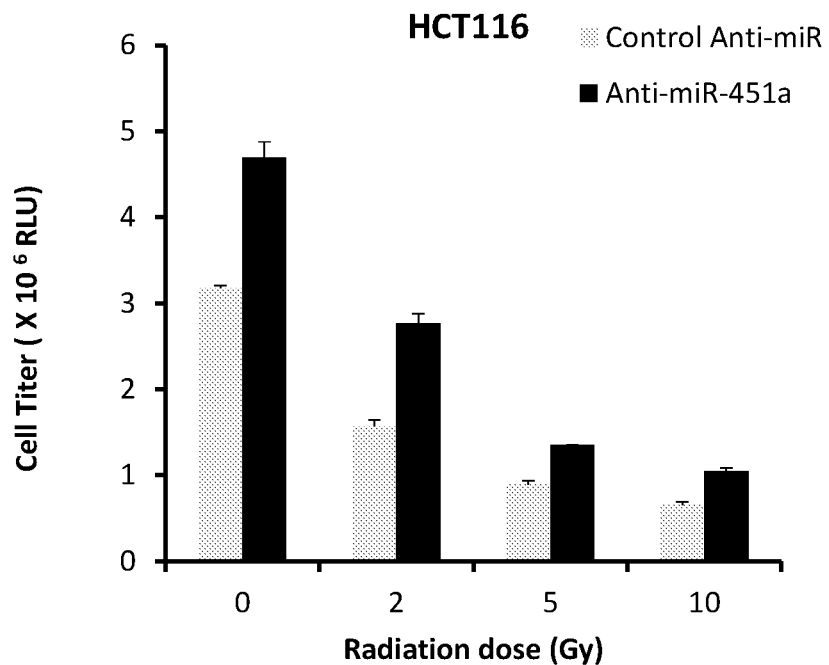
FIG. 3B is a graph showing results where HCT116 were transfected with a miR-451a inhibitor (anti-miR-451a) or a control anti-miR. Proliferation was analyzed 48 hours after radiation in 3D culture with the indicated doses. Bars depict mean±s.e.m. of triplicate wells. ** indicates P<0.01 on a two-tailed Student's T-test.
Figure 3C:
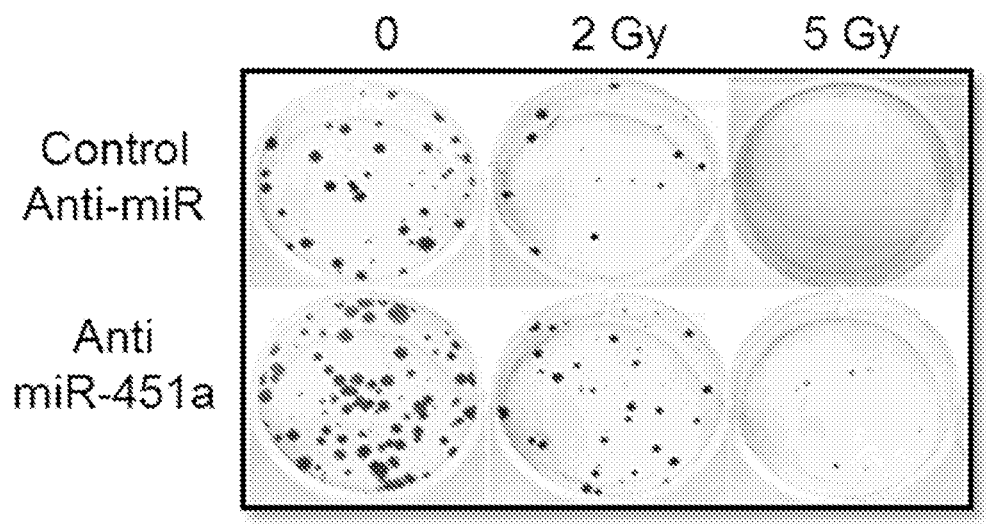
FIG. 3C is an image of the results where 12-14 days after plating, cells were fixed and stained with crystal violet and colonies were counted.
Figure 3D:
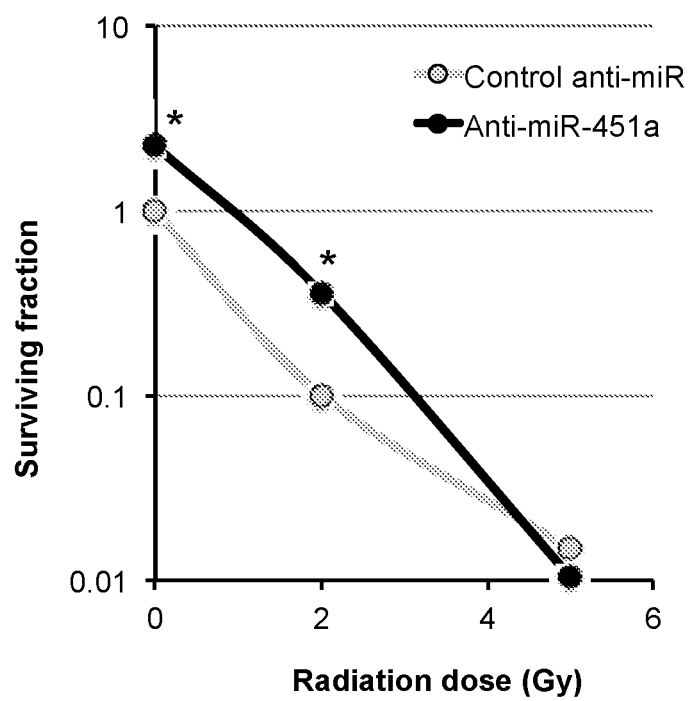
FIG. 3D is a plot of the results shown in FIG. 3C. The surviving fraction was calculated based on the colony numbers normalized to the plating efficiency. The mean of triplicate wells is plotted. * indicates P<0.05 and ** indicates P<0.01 on a two-tailed Student's T-test.
Figure 6A:
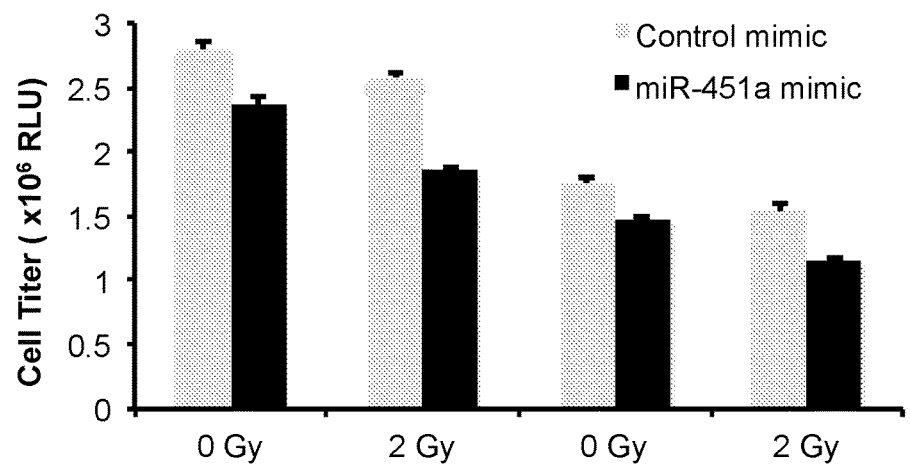
FIG. 6A is a graph of HCT116 transfected with a miR-451a mimic or a control mimic. Proliferation was analyzed 48 hours after radiation and 5-FU (5 μM) treatment. Mean of triplicate wells is plotted. * indicates P<0.01 on a two-tailed Student's T-test.
Figure 6B:
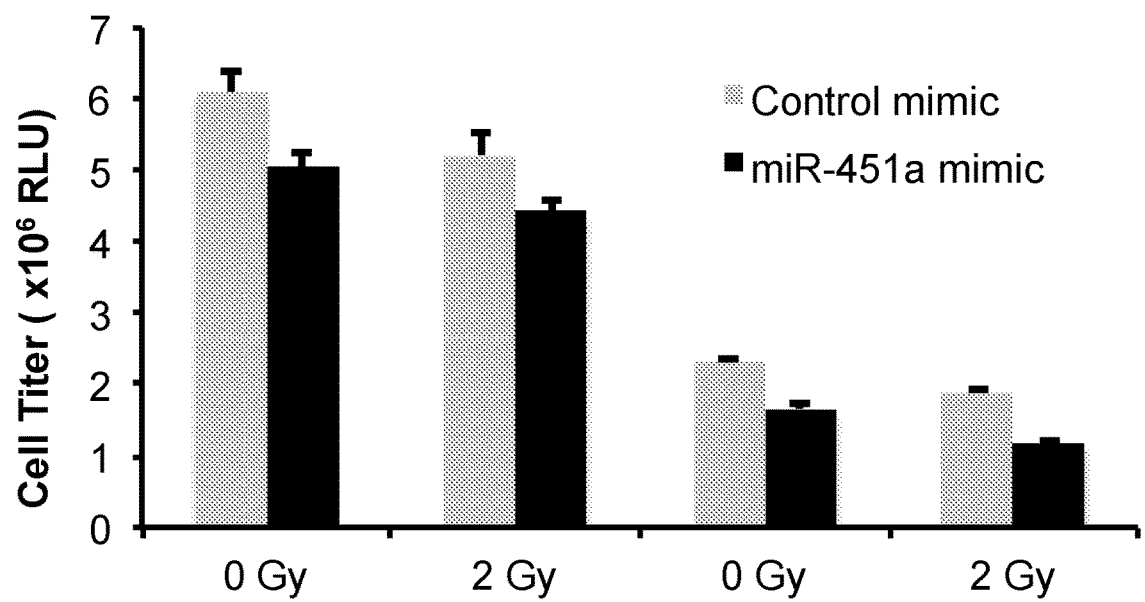
FIG. 6B is a graph of HCT116 transfected with a miR-451a mimic or a control mimic. Proliferation was analyzed 96 hours after radiation and 5-FU (5 μM) treatment. Mean of triplicate wells is plotted. * indicates P<0.01 on a two-tailed Student's T-test FIG. 7 compares the change in HCT-116 proliferation exhibited from treatment with a SHP2 inhibitor, a RAF inhibitor, and the combination of a SHP2 inhibitor and a RAF inhibitor.

Gain of function studies were performed in vitro with HCT-116 cells. Ectopic expression of miR-451a decreased proliferation in a 2D culture (FIG. 2a), a tumorsphere assay and in a surviving fraction colony formation assay (FIG. 2C). It was noted that while miR-451a alone had a significant effect on the phenotypes, there was also slight additive effect with radiation, especially at the 5 Gy dose. Conversely, inhibition of miR-451a enhanced proliferation in 2D (FIG. 3a) and tumorsphere assays (FIG. 3b) almost negating the effects of a 2 Gy dose of radiation. The protection was most robust in the 2 Gy population with a log fold increase in clonogenic survival, but was not evident at higher dose radiation (FIG. 3c). Similar to these findings, miR-451a transfection also enhanced the responses to 5-FU—a commonly used chemosensitizer in colorectal cancer (FIG. 6). Taken together, these studies indicate that miR-451a regulates proliferation of HCT-116 cells.

Example 3—miR-451a Targets Genes Involved in Metabolism and DNA Repair Pathways

Figure 4A:
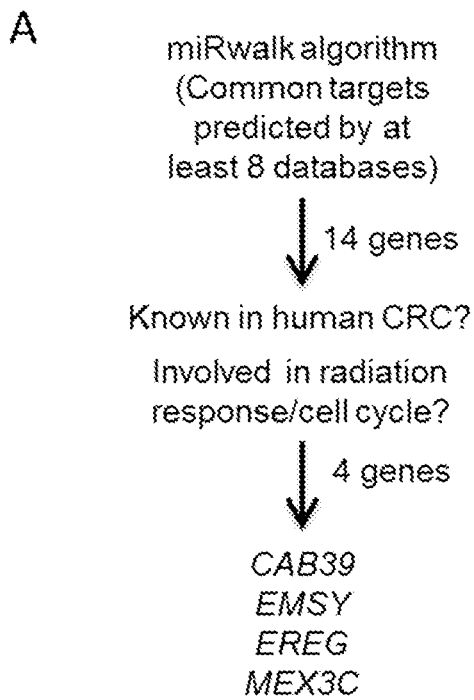
FIG. 4A is a workflow showing how putative miR451a targets were shortlisted based on the predictions of miRwalk algorithm and relevance to human colorectal cancer or radiation.
Figure 4B:
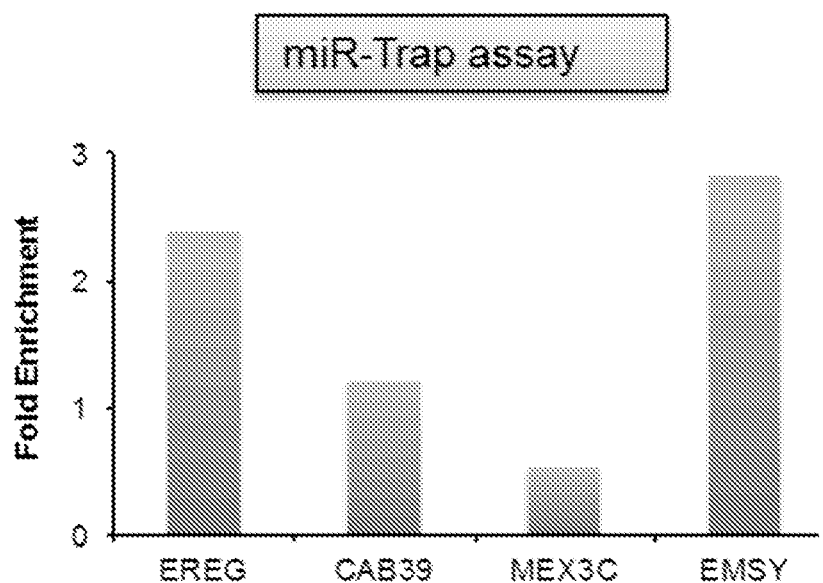
FIG. 4B shows the results of a miR-TRAP assay showing enrichment of target mRNAs immunoprecipitated from HCT116 cells co-transfected with a mutant RISC complex plasmid and a miR-451a mimic or a control miR mimic. Fold enrichment over pre-IP mRNAs is depicted. Results are representative of two independent experiments.
Figure 4C:
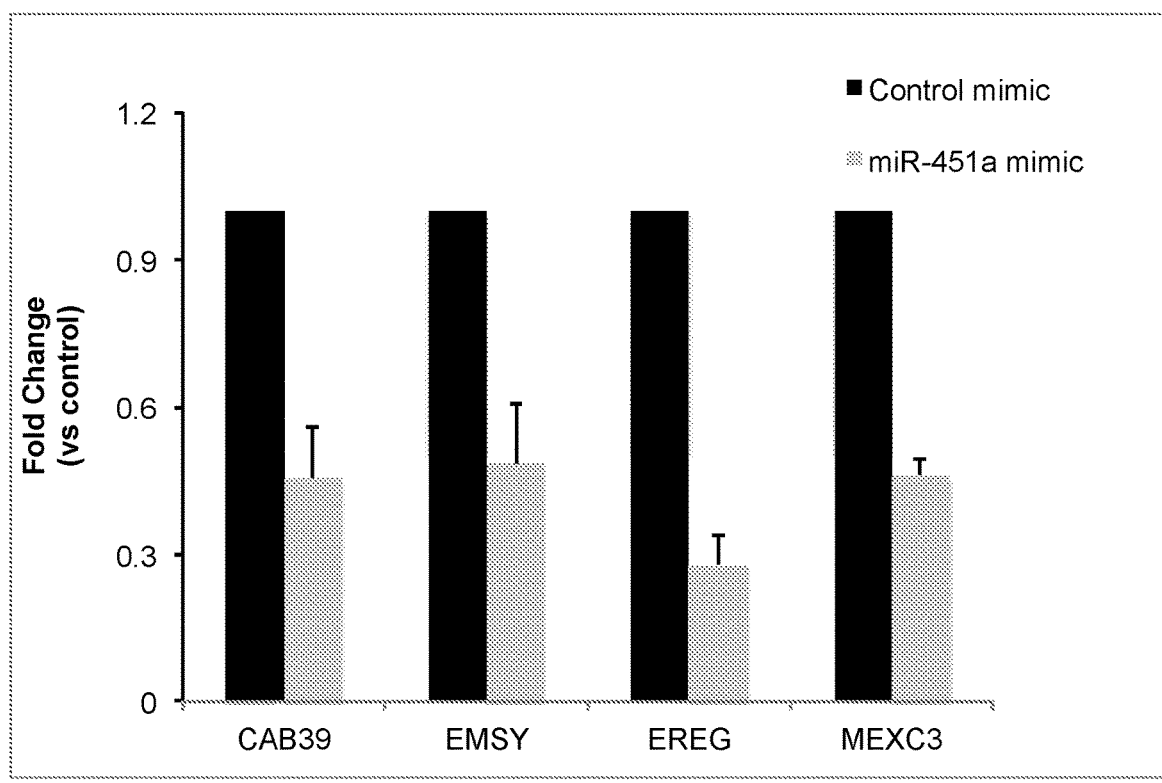
FIG. 4C is a plot of the results of qRT-PCR of the miR-451 targets in HCT-116 cells at 24 h after transfection.

The miRwalk algorithm was used to combine data from multiple target prediction databases and resulted in the identification of 13 genes as putative targets of miR-451a. This list was narrowed by filtering genes with a known role in human colorectal cancer and/or cellular response to ionizing radiation. This resulted in a group of four genes—CAB39, EMSY, EREG, and MEX3C (FIG. 4a). A miR-Trap assay was used to pull down mRNAs enriched at the RNA induced silencing complex in cells transfected with miR-451a. These four target mRNAs were enriched at the RISC (FIG. 4b). Transfection of HCT-116 cells resulted in significant downregulation of all four target genes at the mRNA level (FIG. 4c).

Figure 5A:
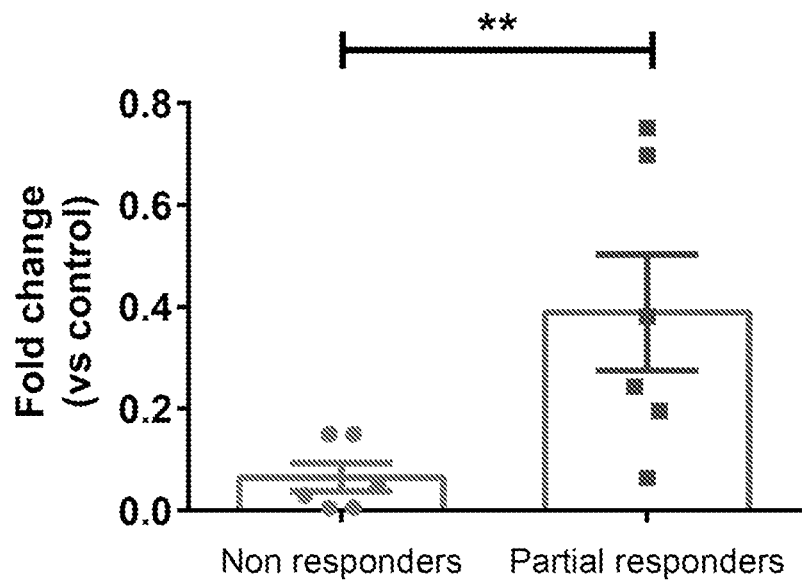
FIG. 5A is a plot of the results of miR-451a levels assayed in rectal cancer patients classified as partial responders (n=6), non-responders (n=6) to chemoradiation as defined by the Mark-Ryne Tumor Regression Score. * indicates P<0.05 and ** indicates P<0.01 on a Mann-Whitney U-test.
Figure 5B:
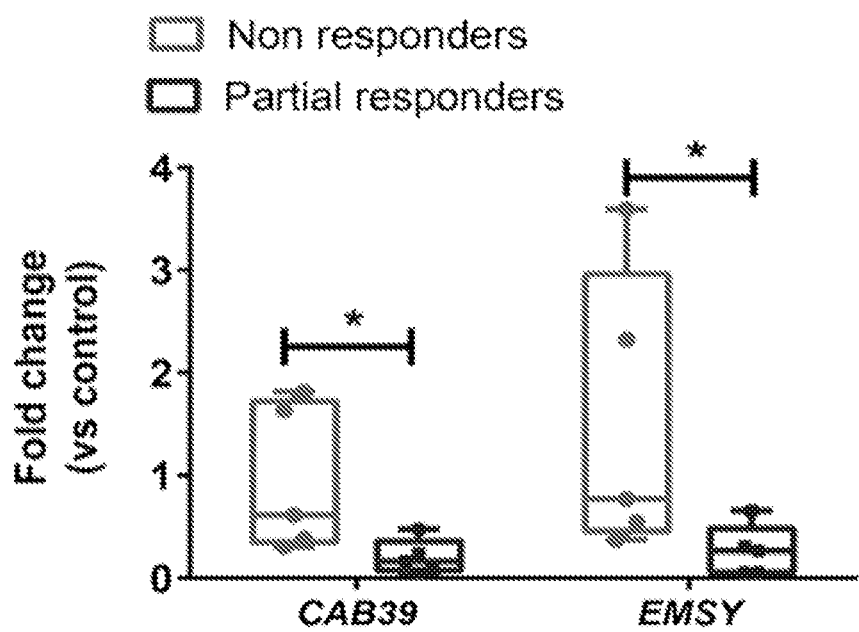
FIG. 5B is a plot of the results of target gene CAB39, EMSY mRNA levels were assayed in rectal cancer patients classified as partial responders (n=6), non-responders (n=6) to chemoradiation as defined by the Mark-Ryne Tumor Regression Score. * indicates P<0.05 and ** indicates P<0.01 on a Mann-Whitney U-test.
Figure 5C:
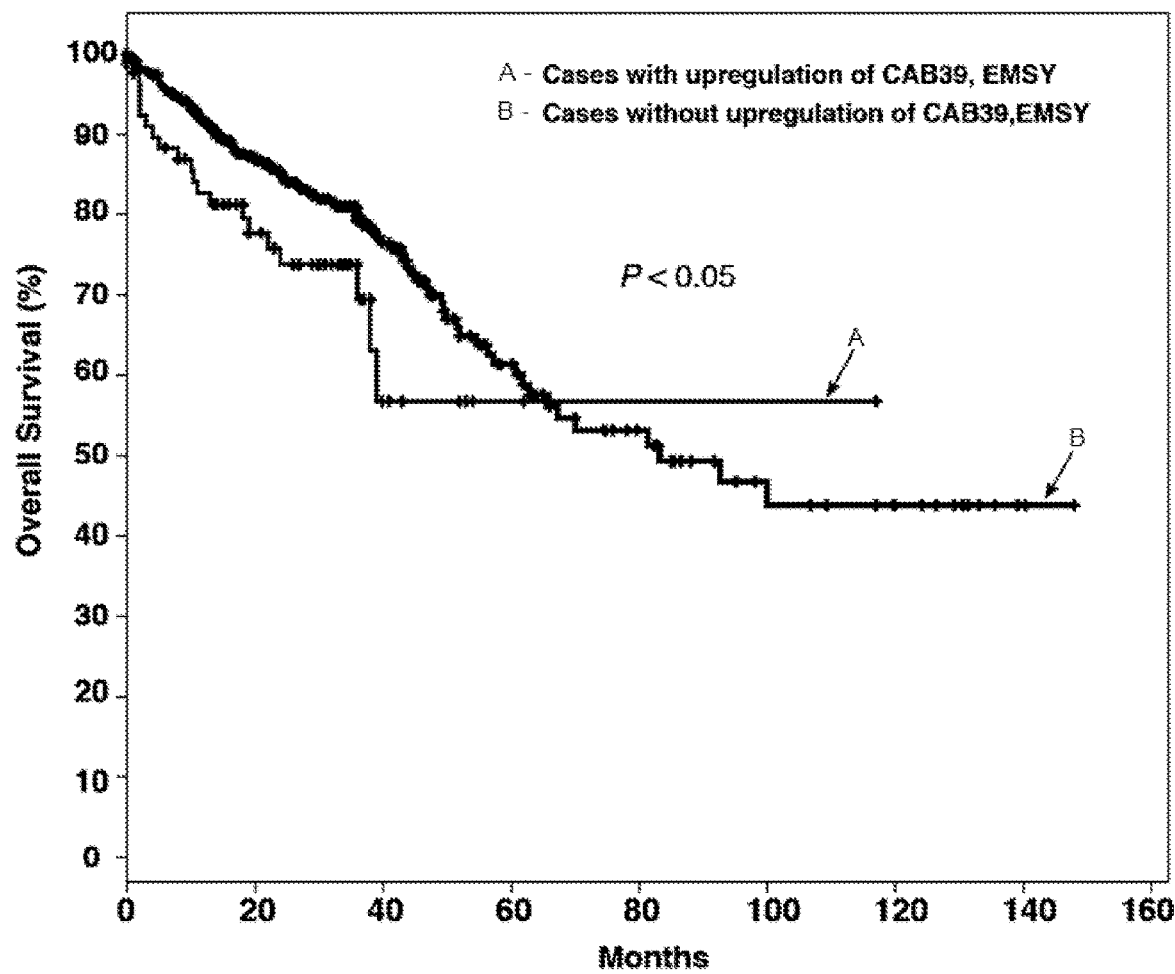
FIG. 5C is a Kaplan Meier plot showing survival of cases with upregulation of CAB39, EMSY compared to the cases without upregulation. P value from a log-rank test.

Example 4—miR-451a and Target Expression Correlates with Chemoradiation Response and Overall Survival in Colorectal Cancer Patients To assess if miR-451a and/or target gene levels were relevant in human colorectal cancer, the miR and target mRNA levels were measured in pre-treatment diagnostic biopsy specimens in rectal cancers from patients who achieved either a partial response (n=6) or no response (n=6) to neoadjuvant chemoradiation. miR-451a was found to be upregulated in partial responders when compared to non-responders (FIG. 5a) and both CAB39 and EMSY levels were downregulated (FIG. 5b). Moreover, analysis of the TCGA database (Provisional colorectal carcinoma, n=639 patients) showed that CAB39 and EMSY protein levels were found to be upregulated in 14% and 6% of cases, respectively (FIG. 5c). Interestingly, upregulated expression of these genes conferred a significantly reduced 3 year overall survival (FIG. 5d).

Example 5—Methods

Affymetrix Analysis:

Affymetrix microRNA array v4.0 profiles were generated by the OHSU Genome Profiling Core facility. Levels of the 2 most upregulated and downregulated 6 h post 2 Gy radiation were validated by qRT-PCR using specific Taqman probes for each microRNA. Mean fold change after normalization to housekeeping RNA, RNU48, is depicted.

Human Rectal Cancer Pathologic Specimens and Extraction:

FFPE diagnostic and pre-treatment biopsy sections from locally advanced rectal cancer patients who underwent standard of care neoadjuvant chemoradiation and subsequent surgical resection were obtained from the OHSU Colorectal Cancer Registry. Patients who demonstrated a greater than 30% decrease in radiologically defined tumor size relative to pre-treatment measurements were defined as partial responses whereas patients with no response to CRT were defined as non-responders. RNA extraction was performed using the Qiagen miRneasy FFPE kit according to manufacturer instructions.

Nanostring miRNA Profiling of Patient Samples:

The Nanostring nCounter Human v3 miRNA Expression Assay Kit was utilized to generate miRNA profiling for 800 human miRNAs in the aforementioned patient tumor samples. Raw quantification of absolute miR counts for each sample were analyzed with background subtraction of the mean negative control miRNAs±2 standard deviations. The miRs were subsequently normalized via implementation of a scaling factor relative to the top 100 expressing miRs among all tested samples. Applied to each specific samples, the geometric means of the top 100 miRs among all tested samples was divided by the corresponding geometric mean for the specific sample.

Cell Culture and Reagents:

HCT-116 cells (ATCC) were cultured in McCoy's supplemented with 10% Fetal Calf Serum and antibiotics. Cells were tested and found negative for mycoplasma contamination before use in the assays described.

Transfections:

HCT-116 cells were reverse transfected with miR-451a-5p mimics, inhibitors and their respective controls were purchased from Life Technologies using Lipofectamine RNAiMAX (Invitrogen) according to manufacturer's instructions.

Colony Formation Assay:

Cells were transfected with miR-451a-5p mimic or control mimic for 16 hours. Then cells were plated (100 or 200 cells for 0Gy, 200 or 400 cells/well for 2GY and 400 or 800 cells per well for 5Gy) in triplicate in a 6-well plate. Cells were irradiated 4 hours after plating, 0Gy, 2Gy or 5Gy. Two weeks after plating, cells were fixed and stained with crystal violet and colonies were counted. Surviving fraction was calculated based on the colony numbers normalized to the plating efficiency.

In Vivo Assays:

All animal work was approved by the OHSU Institutional Animal Use and Care Committee. Immune compromised 8-10 week old nu/nu mice purchased from Jackson Labs were injected subcutaneously with 1 million mycoplasma-negative HCT116 tumor cells in Matrigel (BD) per flank. Tumor growth was measured with calipers, with volume computed as $\frac{1}{2}*Length*Width^2$. Mice were randomized into groups once the average tumor volume reached 80 mm$^3$, approximately 6 days after injection.

Irradiation:

Cells or mice were irradiated on a Shepherd$^{137}$ cesium irradiator at a rate of B166 1.34 cGy min. In tumour-targeted radiation experiments, mice were restrained in a lead shield (Brain Tree Scientific) to minimize exposure to the non-tumour areas.

Cell Titer Glo/Caspase Glo:

HCT-116 cells were transfected in a 6 well plate with miR-451a-5p mimic or inhibitor, and the corresponding controls from Life Technologies as previously described. Cells were transferred to a 96 well plate 16 hours post-transfection (1000 cells/well). At 24 hours post-transfection the HCT-116 cells were irradiated with 0, 2, or 5 Gy. Cell Titer-Glo and Caspase 3/7 Glo were analyzed at 48 hours and 96 hours post-irradiation, according to manufacturer's instructions.

RISC Trap:

HCT116 cells were co-transfected with a plasmid coding for a flag-tagged dominant negative GW418 mutant (Clontech kit #632016) along with a control mimic or miR-451a-5p mimic according to manufacturer instructions. Twenty-four hours later the RNA protein complexes were crosslinked and the RISC complex was immunoprecipitated using an anti-FLAG antibody and RNA was isolated for quantitative real-time PCR of target genes. The fold enrichment was calculated using pre and post IP controls as well as normalization to the control mimic pull-downs.

Example 5

Methods

Patient Selection

Patients were identified with a rectal cancer diagnosis from the years 2000 to 2016 in the Oregon Colorectal Cancer Registry (OCCR) (Gawlick et al., *Am J Surg* 2013; 205:608-612). Patients were categorized as either non-, partial, or complete pathological responders, based on a pathological tumor regression score. Non-responders had greater than 50% tumor, partial responders had less than 50%, and complete responders were identified with either no or small singular cancer cells remaining on pathologic review (Gibbons et al., *Histopathol* 2005; 47:141-146).

Tissue Collection

Pre-treatment and post-treatment specimens were obtained at the time of diagnosis and prepared on 5 µm thick fixed paraffin-embedded (FFPE) specimen slides, which were independently assessed by two pathologists. Post-treatment specimens were obtained following standard CRT and surgical resection. Pre-treatment specimens were used for miR profiling, and post-treatment surgical FFPE specimens were used for confirmatory quantitative PCR (qPCR) analysis. In patients with complete response, the tumor bed was identified by scar tissue, which was utilized for analysis. Macrodissection of slides was utilized. Slides containing greater than 20% necrosis, or less than 50% tumor were not utilized for study. Plasma samples were collected at the time of surgery and stored at −80° C.

RNA Isolation miRs were isolated from FFPE patient slides, using an RNeasy FFPE Kit (Qiagen catalog #73504). miRs were isolated from patient plasma, using mirRNeasy Plasma/Serum Kit (Qiagen catalog #217184). cDNA synthesis was performed, utilizing the High Capacity cDNA Reverse Transcription kit (Applied Biosystems, Catalog #4368814). For miR cDNA synthesis, specific miR primers were used, following the TaqMan™ Small RNA Assay Protocol. qPCR was performed with the TaqMan® Gene Expression Assays (Applied Biosystems), using the Applied Biosystems ViiA7 qRT-PCR instrument. miR values were normalized to qPCR reactions performed in quadruplicate. miR values were normalized to the Lifetech probes and primers (housekeeping control RNU48 or GAPDH, Life Technologies), using the delta delta CT method (Schmittgen et al., *Nat Protoc* 2008; 3:1101-1108).

MicroRNA Profiling miRs isolated from twelve pre-treatment FFPE specimens of six non- and six partial responders were compared using the NanoString Technology platform. 3 uL of RNA were added to miRNA tag ligation reaction with reporter and capture probes. Raw counts for each assay were collected using NanoString's data analysis application, nSolver™. Normalization of the data was carried out using the NanoString nSolver™ analysis application, and each assay was normalized based on the mean counts of the 100 most-abundant miRNA. A total of 798 human miRs were profiled. Upregulated and downregulated miRs with differences higher than 1.5 fold between groups were identified. Among these 14 candidate miRs, those significantly altered in CRC were the focus of further investigation.

Downstream Target Analysis

Using the Cancer Genome Atlas (TCGA) data, downstream targets of miR-451a in CRC tumors were assessed (The Cancer Genome Atlas 2015; https://cancergenome.nih.gov/. Accessed Mar. 24, 2017, 2017). SurvExpress, an online biomarker validation for cancer gene expression tool, was used to better understand the target expression profiles.

In Vitro Models

HCT-116 cells (American Type Culture Collection) were cultured in McCoy's media supplemented with 10% fetal bovine serum (FBS) and antibiotics. Cells were tested and found negative for mycoplasma contamination before use in the assays described. Cells were reverse transfected with miR-451a-5p mimics or inhibitors with their respective controls (purchased from Life Technologies), using Lipofectamine® RNAiMAX (Invitrogen) per manufacturer's instructions. We report highly efficient transfection (>90%) of mimics and inhibitors in cell culture, as measured by fluorescent miR control. Cells were irradiated in a Shepherd[137] cesium irradiator at a rate of 1.34 cGy min. HCT-116 cells were initially transfected in a six-well plate, then transferred to a 96-well plate 16 hours post-transfection (2000 cells/well). In the chemosensitivity model, HCT-116 cells were treated with SHP2 inhibitor SHP099, 6-(4-diamino-4-methyl-1-piperidinyl)-3-(2,3-dichlorophenyl)-2-pyrazinamine (Cayman Chemical, cat#20000) (3.5 µM), and RAF inhibitor (selective paradox breaker; SelleckChem, PLX7904, N'-[3-[[5-(2-cyclopropyl-5-pyrimidinyl)-1H-pyrrolo[2,3-b]pyridin-3-yl]carbonyl]-2,4-difluorophenyl]-N-ethyl-N-methyl-sulfamide, cat#57964) (20 µM) at 24 hours post transfection. Cell proliferation was analyzed at 48 hours post irradiation, using CellTiter-Glo®, per the manufacturer's instructions.

Statistical Analysis

Clinicopathological data was collected, and response groups were compared, using Chi-square tests and the Freeman-Halton extension of Fisher's Exact test. NanoString profiling was performed by a NanoString proof of concept study. De-identified specimens were sent to NanoString and data were returned normalized per standard protocol. Differences in gene expression determined by qPCR among pathological non-, partial, and complete responders groups were evaluated with Mann-Whitney tests. Correlations were calculated between miR-451a and downstream genes stratified by response to chemoradiotherapy (CRT). Differences in serum treatment groups were evaluated with exact F-tests from a multivariate ANOVA. A significant difference was declared if the p-value was less than or equal to 0.05. Marginal significance was declared if the p-value was greater than 0.05, but less than or equal to 0.10. All analyses were completed with JMP® 13 and SAS® 9.4 (SAS Institute Inc.).

Results

We examined 45 patients who underwent treatment for rectal cancer from 2000 to 2016 captured in the OCCR with available tissue for exploratory analysis. There were a total of 13 non-responders, 18 partial responders, and 14 complete responders. For three patients, demographic data was not available. The level of response was significantly different across pathological T-stage and marginally significant for M-stage patients.

Using NanoString profiling, we identified four up-regulated miRs, miR-451a, 502-5p, 223-3p, and 1246 (>1.5 fold change), table below. Included are the following miRs with their miRbase Accession Number as of Jan. 5, 2018: hsa-miR-200b-3p (MI0000342), hsa-miR-202-3p (MIMAT0002811), hsa-miR-223-3p (MIMAT0000280), hsa-miR-23a-3p (MIMAT0000078), hsa-miR-376b-3p (MIMAT0002172), hsa-miR-455-3p (MIMAT0004784), hsa-miR-502-5p (MIMAT0002873), hsa-miR-548ar-5p (MIMAT0002265), hsa-miR-575 (MI0003582), hsa-miR-603 (MI0003616), hsa-miR-627-5p (MIMAT0003296), hsa-miR-1246 (MI0006381), and hsa-miR-1253 (MI0006387).

| miR | Fold Change (PR vs NR) |
|---|---|
| hsa-miR-200b-3p | 1.5667** |
| hsa-miR-202-3p | 1.6242** |
| hsa-miR-223-3p | 1.7935** |
| hsa-miR-23a-3p | 1.6358** |
| hsa-miR-376b-3p | 1.5160** |
| hsa-miR-451a | 1.7147** |
| hsa-miR-455-3p | 0.4384* |
| hsa-miR-502-5p | 2.0850** |
| hsa-miR-548ar-5p | 0.3672* |
| hsa-miR-575 | 1.5363** |
| hsa-miR-603 | 0.3827* |
| hsa-miR-627-5p | 0.4116* |
| hsa-miR-1246 | 1.9220** |
| hsa-miR-1253 | 0.0675* |

*corresponds to down regulation,
**corresponds to up regulation

Prior data demonstrated significant influence of miR-451a in colorectal cancer in vitro and in vivo models (Ruhl et al., bioRxiv 136234 May 10, 2017). miR-451a was validated in our cohort out of the four miRs upregulated due to these prior findings. Exploration of post-treatment tissue was completed, using qPCR. There was no significant difference between non- or partial responders; there was, however, a slight increase in expression of miR-451a in the partial responders. Patient-matched post-treatment plasma was also assessed for miR-451a, and expression was higher in the complete responders versus non-responders and partial responders.

Prior in vitro and in vivo models demonstrated miR-451a directly binds and downregulates CAB39 and EMSY(Ruhl et al., bioRxiv 136234 May 10, 2017). These two proteins are expressed in 14% and 6% of CRC, which was associated with worse survival. The expression profile of CAB39 and EMSY in our patient cohort demonstrated a non-significant increase in the non-responders, when compared to partial and complete responders. Results of tissue and plasma expression of miR-451a and genes are summarized in the table below.

PCR quantification of posttreatment tissue and plasma expression of miR-451a and genes CAB39 and EMSY are summarized in the table below.

| | | | Response | | |
|---|---|---|---|---|---|
| miR | Total (n = 45) | % None (n = 13) | Partial (n = 18) | Complete (n = 14) | P |
| miR-451a | | | | | |
| Tissue (mean Δ-CT, SD) | 43 | 0.0747 (0.1163) | 0.1275 (.2122) | 0.1748 (.3818) | 0.2111* |
| Plasma (mean Δ-CT, SD) | 17 | 1.8878 (1.7501) | 1.5567 (1.1662) | 5.6908 (6.4993) | 0.6437* |
| CAB39 (mean Δ-CT, SD) | 35 | 0.5109 (0.6180) | 0.2082 (.1524) | 0.2360 (.1836) | 0.4820* |
| EMSY (mean Δ-CT, SD) | 37 | 0.6875 (1.185) | 0.1326 (.1804) | 0.1541 (.2134) | 0.5275* |

*Mann-Whitney test

Figure 7:
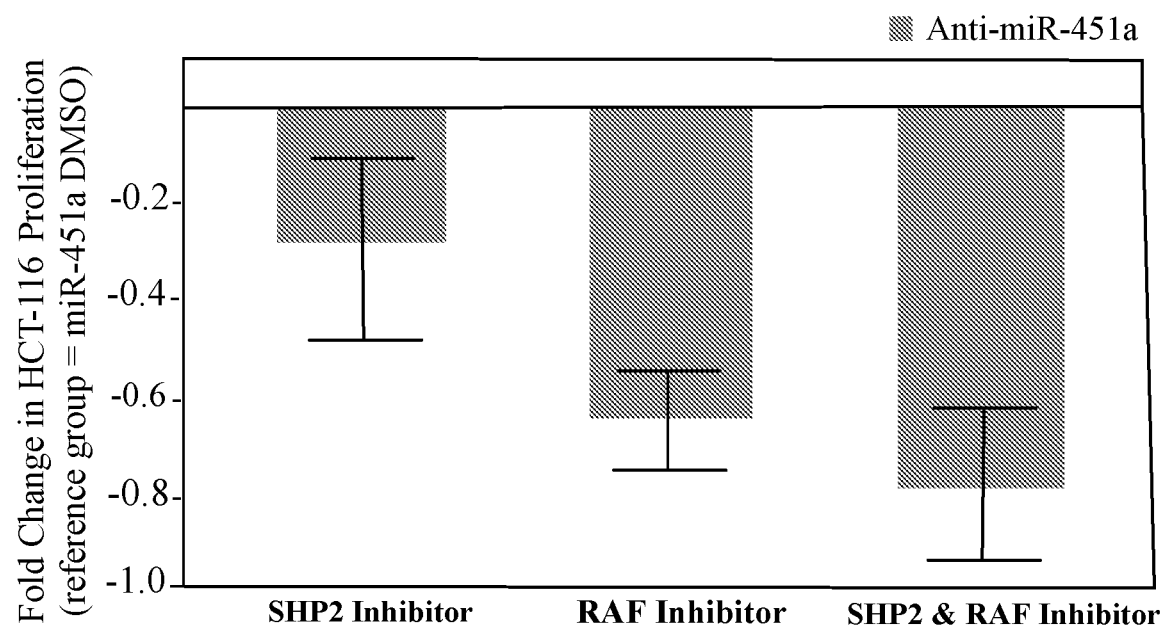

CAB39 and EMSY proteins are correlated with poorer overall survival. Patients with increased CAB39 and EMSY are shown to have upregulation in a number of signaling pathways, including RAF kinases and SHP2 enzymes. We have demonstrated miR-451a directly binds and downregulates CAB39 and EMSY (Ruhl R K K, Espinosa-Diez C, Hudson C, Lanciault C, Tsikitis V L, Anand S. microRNA-451a regulates colorectal cancer radiosensitivity. bioRxiv 136234 May 10, 2017). We inhibited RAF and SHP2 in HCT-116 cells reverse transfected with anti-miR-451a. We found cells treated with SHP2 and RAF inhibitors demonstrated a significant decrease in cell proliferation. Specifically, the combined treatment of 20 uM RAF-inhibitor and 3.5 uM SHP2-inhibitor was the most effective at preventing cell proliferation (p<0.0001) (FIG. 7).

We find that downstream genes CAB39 and EMSY are controlled by miR451a and may be targeted by treatment with SHP2 and RAF inhibitors in human subjects with low miR451a expression levels who are experiencing rectal cancer and who may have a limited response to CRT.

As such, for each of the methods of treatment described herein there is a further embodiment further comprising administering to a subject in need thereof a therapeutically effective amount of a RAF inhibitor, a SHP2 inhibitor, or a combination of a RAF inhibitor and a SHP2 inhibitor.

Also provided is a kit for sensitizing colorectal cancer cells in a subject to radiation, the kit comprising:
  a) a therapeutically effective amount of miR-451a (SEQ ID NO: 1);
  b) a therapeutically effective amount of a RAF inhibitor, a SHP2 inhibitor, or a combination of a RAF inhibitor and a SHP2 inhibitor; and
  c) instructions for using the miR-451a and the RAF inhibitor, SHP2 inhibitor, or combination of a RAF inhibitor and a SHP2 inhibitor to sensitize colorectal cancer cells in a subject to radiation.

Examples of RAF inhibitors that may be used include vemurafenib, sorafenib, dabrafenib, lifirafenib (BGB-283), encorafenib (LGX818), PLX-4720 (N-(3-(5-chloro-1H-pyrrolo[2,3-b]pyridine-3-carbonyl)-2,4-difluorophenyl)propane-1-sulfonamide), GDC-0879 ((E)-5-(1-(2-hydroxyethyl)-3-(pyridin-4-yl)-1H-pyrazol-4-yl)-2,3-dihydroinden-1-one oxime), CCT196969 (N-[4-[(3,4-dihydro-3-oxopyrido[2,3-b]pyrazin-8-yl)oxy]-2-fluorophenyl]-N'-[3-(1,1-dimethylethyl)-1-phenyl-1H-pyrazol-5-yl]-urea), RAF265 (CHIR-265, 1-methyl-5-(2-(5-(trifluoromethyl)-1H-imidazol-2-yl)pyridin-4-yloxy)-N-(4-(trifluoromethyl) phenyl)-1H-benzo[d]imidazol-2-amine), AZ 628 (3-(2-cyanopropan-2-yl)-N-(4-methyl-3-(3-methyl-4-oxo-3,4-dihydroquinazolin-6-ylamino)phenyl)benzamide), SB590885 ((E)-5-(2-(4-(2-(dimethylamino)ethoxy)phenyl)-4-(pyridin-4-yl)-1H-imidazol-5-yl)-2,3-dihydroinden-1-one oxime), ZM 336372 (3-(dimethylamino)-N-[3-[(4-hydroxybenzoyl)amino]-4-methylphenyl]-benzamide), GW5074 (3-[(3,5-dibromo-4-hydroxyphenyl)methylene]-1,3-dihydro-5-iodo-2H-indol-2-one), TAK-632 (N-(7-cyano-6-(4-fluoro-3-(2-(3-(trifluoromethyl)phenyl)acetamido) phenoxy)benzo[d]thiazol-2-yl)cyclopropanecarboxamide), PLX7904 (N'-[3-[[5-(2-cyclopropyl-5-pyrimidinyl)-1H-pyrrolo[2,3-b]pyridin-3-yl]carbonyl]-2,4-difluorophenyl]-N-ethyl-N-methyl-sulfamide), LY3009120 (1-(3,3-dimethylbutyl)-3-(2-fluoro-4-methyl-5-(7-methyl-2-(methyl amino)pyrido[2,3-d]pyrimidin-6-yl)phenyl)urea), RO5126766 (CH5126766, 3-{2-(methylaminosulfonyl)amino-3-fluoropyridin-4-ylmethyl}-4-methyl-7-(pyrimidin-2-yloxy)-2-oxo-2H-1-benzopyran), MLN2480 (6-amino-5-chloro-N-[(1R)-1-[5-[[[5-chloro-4-(trifluoromethyl)-2-pyridinyl]amino]carbonyl]-2-thiazolyl]ethyl]-4-Pyrimidinecarboxamide).

Examples of SHP2 inhibitors that may be used in the methods herein include TN0155, SHP099 (6-(4-amino-4-methylpiperidin-1-yl)-3-(2,3-dichlorophenyl)pyrazin-2-amine), NAT6-297775, NSC-87877 (8-hydroxy-7-[(6-sulfo-2-naphthalenyl)azo]-5-Quinolinesulfonic acid), II-B08 (3-(1-(3-(Biphenyl-4-ylamino)-3-oxopropyl)-1H-1,2,3-tirazol-4-yl)-6-hydroxy-1-methyl-2-phenyl-1H-indole-5-carboxylic acid, fumosorinone, SPI-112 (3-[(2Z)-2-[5-[[[(4-fluorophenyl) methyl]amino]sulfonyl]-1,2-dihydro-2-oxo-3H-indol-3-ylidene]hydrazinyl]-benzoic acid, as well as its methyl ester, SPI-112-Me), PHPS1 (4-(N'-(3-(4-Nitrophenyl)-5-oxo-1-phenyl-1,5-dihydro-pyrazol-(4Z)-ylidene)-hydrazino)-benzenesulfonic acid), C21, tautomycetin, TTN D-1,7-deshydroxypyrogallin-4-carboxylic acid (DCA), and the SHP2 inhibiting compounds disclosed in WO 2016203404 (Bagdanoff et al.), WO 2016203405 (Chen et al.), WO 2016203406 (Chen et al.), US 20150352131 (Yang et al.), WO 2016196591 (Zhang et al.), CN 107286150 (Zhu et al.), CN 102432544 (Cheng et al.), WO 2015107493 (Chen et al.), WO 2015107494 (Chen et al.), WO 2015107495 (Chen et al.), KR 1373912 (Cho et al.), U.S. Pat. No. 8,623,906 (Wu et al.), U.S. Pat. No. 9,174,969 (Wu et al.), U.S. Pat. No. 7,868,185 (Birchmeier et al.), U.S. Pat. No. 7,439,249 (Saunders et al.) U.S. 20170204080 (Chen et al.), and WO 2016151501 (Buschmann et al).

The invention claimed is:

1. A method of sensitizing colorectal cancer cells in a subject to ionizing radiation, the method comprising administering to a subject in need thereof an effective amount of miR-451a (SEQ ID NO: 1).

2. A method of treating colorectal cancer in a subject, the method comprising:
sensitizing colorectal cancer cells in the subject to ionizing radiation by administering to the subject in need thereof an effective amount of miR-451a (SEQ ID NO: 1) such that the miR-451a is present and/or expressed within the colorectal cancer cells; and
administering a dose of at least 1Gy of ionizing radiation to the colorectal cancer cells in the subject.

3. The method of claim 2, further comprising administering to the subject in need thereof one or more therapeutically effective doses of 5-fluorouracil.

4. The method of claim 3, wherein the one or more therapeutically effective doses of 5-fluorouracil are administered at an individual dose of from about 100 mg/m$^2$ to about 2,000 mg/m$^2$.

5. The method of claim 3, wherein the one or more therapeutically effective doses of 5-fluorouracil are administered at an individual dose of from about 150 mg/m$^2$ to about 300 mg/m$^2$.

6. The method of claim 3, wherein the one or more therapeutically effective doses of 5-fluorouracil are administered at an individual dose of from about 200 mg/m$^2$ to about 250 mg/m$^2$.

7. The method of claim 2, further comprising administering to the subject in need thereof one or more therapeutically effective doses of a chemotherapeutic agent selected from the group of capecitabine, Irinotecan, oxaliplatin, and trifluridine and tipiracil.

8. The method of claim 2, further comprising administering to the subject in need thereof one or more therapeutically effective doses of an agent selected from the group of bevacizumab, ramucirumab, and ziv-aflibercept, cetuximab, panitumumab, and regorafenib.

9. The method of claim 2, wherein the source of the ionizing radiation comprises a beta-emitter.

10. The method of claim 2, further comprising administering to the subject in need thereof a therapeutically effective amount of a RAF inhibitor, a SHP2 inhibitor, or a combination of a RAF inhibitor and a SHP2 inhibitor.

11. The method of claim 2, wherein the colorectal cancer is an adenocarcinoma.

12. The method of claim 2, wherein the effective amount of miR-451a (SEQ ID NO: 1) is from about 0.1 mg/kg to about 20 mg/kg.

13. The method of claim 2, wherein the effective amount of miR-451a (SEQ ID NO: 1) is from about 0.1 mg/kg to about 15 mg/kg.

14. The method of claim 2, wherein the effective amount of miR-451a (SEQ ID NO: 1) is from about 0.1 mg/kg to about 10 mg/kg.

15. The method of claim 2, wherein the effective amount of miR-451a (SEQ ID NO: 1) is from about 0.1 mg/kg to about 5 mg/kg.

* * * * *